United States Patent
Feng et al.

(10) Patent No.: US 11,642,329 B2
(45) Date of Patent: *May 9, 2023

(54) AMORPHOUS SOLID FORM OF COMPOUNDS CONTAINING S—N-VALERYL-N- {[2'-( 1 H-TETRAZOLE-5-YL)-BIPHENYL-4-YL]-METHYL}-VALINE AND (2R,4S)-5-BIPHENYL-4-YL-4-(3-CARBOXY-PROPIONYLAMINO)-2-METHYL-PENTANOIC ACID ETHYL ESTER MOIETIES AND SODIUM CATIONS

(71) Applicant: Novartis Pharmaceuticals Corporation, East Hanover, NJ (US)

(72) Inventors: Lili Feng, Pine Brook, NJ (US); Sven Erik Godtfredsen, Chatham, NJ (US); Paul Allen Sutton, Getzville, NY (US); Mahavir Prashad, Montville, NJ (US); Michael J. Girgis, Montville, NJ (US); Bin Hu, Green Brook, NJ (US); Yugang Liu, Warren, NJ (US); Thomas J. Blacklock, East Hanover, NJ (US); Piotr Henryk Karpinski, Lincoln Park, NJ (US)

(73) Assignee: Novartis Pharmaceuticals Corporation, East Hanover, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/847,588

(22) Filed: Jun. 23, 2022

(65) Prior Publication Data

US 2022/0331282 A1    Oct. 20, 2022

Related U.S. Application Data

(60) Continuation of application No. 17/395,305, filed on Aug. 5, 2021, which is a division of application No. (Continued)

(51) Int. Cl.
  *A61K 31/216* (2006.01)
  *A61K 31/41* (2006.01)
  (Continued)

(52) U.S. Cl.
  CPC .......... *A61K 31/216* (2013.01); *A61K 31/41* (2013.01); *A61K 31/4422* (2013.01);
  (Continued)

(58) Field of Classification Search
  CPC .......................... C07C 233/47; C07D 257/04
  See application file for complete search history.

(56) References Cited

U.S. PATENT DOCUMENTS

| | | | |
|---|---|---|---|
| 1,954,909 A | 4/1934 | Oscar et al. | |
| 2,499,058 A | 2/1950 | Cusic | |

(Continued)

FOREIGN PATENT DOCUMENTS

| | | |
|---|---|---|
| CA | 2055683 A1 | 5/1992 |
| CA | 2472399 A1 | 7/2003 |

(Continued)

OTHER PUBLICATIONS

Waeber, Bernard and Feihl, Francois, The Lancet, "Blood pressure reduction with LCZ696" Mar. 16, 2010, vol. 375 No. 97222 pp. 1228-1229.

(Continued)

*Primary Examiner* — Timothy P Thomas
(74) *Attorney, Agent, or Firm* — Timothy P. O'Dea

(57) ABSTRACT

An amorphous solid form of a compound comprising of the angiotensin receptor antagonist (ARB) valsartan, the neutral endopeptidase inhibitor (NEPi) (2R,4S)-5-biphenyl-4-yl-4-(3-carboxy-propionylamino)-2-methylpentanoic acid ethyl ester and sodium cations is provided. This is compound is useful for the treatment of hypertension and/or heart failure.

2 Claims, 1 Drawing Sheet

Related U.S. Application Data

16/579,581, filed on Sep. 23, 2019, now Pat. No. 11,096,918, which is a continuation of application No. 16/006,252, filed on Jun. 12, 2018, now abandoned, which is a continuation of application No. 15/187,872, filed on Jun. 21, 2016, now abandoned, which is a division of application No. 14/311,788, filed on Jun. 23, 2014, now Pat. No. 9,388,134, which is a division of application No. 11/722,360, filed as application No. PCT/US2006/043710 on Nov. 8, 2006, now Pat. No. 8,877,938.

(60) Provisional application No. 60/822,086, filed on Aug. 11, 2006, provisional application No. 60/789,332, filed on Apr. 4, 2006, provisional application No. 60/735,541, filed on Nov. 10, 2005, provisional application No. 60/735,093, filed on Nov. 9, 2005.

(51) Int. Cl.
*C07C 233/47* (2006.01)
*C07D 257/04* (2006.01)
*A61K 45/06* (2006.01)
*A61K 31/4422* (2006.01)
*A61K 31/5415* (2006.01)
*C07D 207/50* (2006.01)

(52) U.S. Cl.
CPC .......... *A61K 31/5415* (2013.01); *A61K 45/06* (2013.01); *C07C 233/47* (2013.01); *C07D 207/50* (2013.01); *C07D 257/04* (2013.01); *A61K 2300/00* (2013.01)

(56) References Cited

U.S. PATENT DOCUMENTS

| | | |
|---|---|---|
| 2,534,813 A | 12/1950 | Cusic |
| 3,057,731 A | 10/1962 | Ingemar |
| 4,610,816 A | 9/1986 | Berger |
| 4,722,810 A | 2/1988 | Delaney et al. |
| 4,740,499 A | 4/1988 | Olins |
| 4,749,688 A | 6/1988 | Haslanger et al. |
| 4,929,641 A | 5/1990 | Haslanger et al. |
| 5,217,996 A | 6/1993 | Ksander |
| 5,223,516 A | 6/1993 | Delaney et al. |
| 5,225,401 A | 7/1993 | Seymour |
| 5,250,522 A | 10/1993 | De Lombaert |
| 5,273,990 A | 12/1993 | De Lombaert |
| 5,294,632 A | 3/1994 | Erion et al. |
| 5,376,293 A | 12/1994 | Johnston |
| 5,399,578 A | 3/1995 | Buhlymayer et al. |
| 5,520,522 A | 5/1996 | Rathore et al. |
| 6,248,729 B1 | 6/2001 | Coniglio et al. |
| 6,262,092 B1 | 7/2001 | Chang et al. |
| 6,693,216 B2 | 2/2004 | Raczek et al. |
| 6,737,430 B2 | 5/2004 | Crook et al. |
| 6,869,970 B2 | 3/2005 | Marti |
| 8,877,938 B2 | 11/2014 | Feng et al. |
| 2002/0098241 A1 | 7/2002 | Venkatesh |
| 2004/0138274 A1 | 7/2004 | Dack et al. |
| 2004/0242661 A1 | 12/2004 | Rukhman et al. |
| 2005/0070551 A1 | 3/2005 | Remenar et al. |
| 2005/0165075 A1 | 7/2005 | Parthasaradhi et al. |
| 2009/0299056 A1 | 12/2009 | Wang et al. |

FOREIGN PATENT DOCUMENTS

| | | |
|---|---|---|
| CN | 1061404 A | 5/1992 |
| CN | 1097576 A | 1/1995 |
| CN | 1397556 A | 2/2003 |
| CN | 1513854 A | 7/2004 |
| CN | 1603326 A | 4/2005 |
| CN | 1651433 A | 8/2005 |
| CN | 1246482 C | 3/2006 |
| CN | 1793147 A | 6/2006 |
| CN | 105037289 A | 11/2015 |
| CN | 105503760 A | 4/2016 |
| CN | 105873586 | 8/2016 |
| CN | 106905253 A | 6/2017 |
| CN | 107674038 A | 2/2018 |
| CN | 109912525 A | 6/2019 |
| EP | 0034172 B1 | 5/1983 |
| EP | 0342850 A1 | 11/1989 |
| EP | 0343911 A2 | 11/1989 |
| EP | 0361365 A1 | 4/1990 |
| EP | 0443983 A1 | 8/1991 |
| EP | 0498361 A2 | 8/1992 |
| EP | 0509442 A1 | 10/1992 |
| EP | 0590442 A1 | 4/1994 |
| EP | 0636621 A1 | 2/1995 |
| EP | 0726072 A2 | 8/1996 |
| EP | 1948158 B1 | 7/2008 |
| EP | 3272734 A1 | 1/2018 |
| GB | 2218983 A | 11/1989 |
| IN | 201641010897 A | 12/2017 |
| IN | 201811000274 A | 8/2019 |
| IN | 201621044625 A | 12/2019 |
| JP | 6-234754 A | 8/1994 |
| JP | 7-157459 A | 6/1995 |
| WO | 9009374 A1 | 8/1990 |
| WO | 9213564 A1 | 8/1992 |
| WO | 9214706 A1 | 9/1992 |
| WO | 9309101 A1 | 5/1993 |
| WO | 9310773 A1 | 6/1993 |
| WO | 9415908 A1 | 7/1994 |
| WO | 00/02543 A2 | 1/2000 |
| WO | 00/73271 A1 | 12/2000 |
| WO | 00/73298 A1 | 12/2000 |
| WO | 0174348 A2 | 10/2001 |
| WO | 02/06253 A1 | 1/2002 |
| WO | 0206253 A1 | 1/2002 |
| WO | 0240007 A1 | 5/2002 |
| WO | 02/083066 A2 | 10/2002 |
| WO | 02092622 A2 | 11/2002 |
| WO | 03/035046 A2 | 5/2003 |
| WO | 03059345 A1 | 7/2003 |
| WO | 03066606 A1 | 8/2003 |
| WO | 03/074474 A2 | 9/2003 |
| WO | 03/089417 A1 | 10/2003 |
| WO | 03/094915 A1 | 11/2003 |
| WO | 03/097098 A1 | 11/2003 |
| WO | 03097045 A1 | 11/2003 |
| WO | 2004078161 A1 | 9/2004 |
| WO | 2004078163 A2 | 9/2004 |
| WO | 2004083192 A1 | 9/2004 |
| WO | 2004101535 A1 | 11/2004 |
| WO | 2005049587 A1 | 6/2005 |
| WO | 2006086456 A2 | 8/2006 |
| WO | 2007056546 A1 | 5/2007 |
| WO | 03059345 A1 | 7/2013 |
| WO | 2016037552 A1 | 3/2016 |
| WO | 2016049663 A1 | 3/2016 |
| WO | 2016125123 A1 | 8/2016 |
| WO | 2016201238 A1 | 12/2016 |
| WO | 2017009784 A1 | 1/2017 |
| WO | 2017042700 A1 | 3/2017 |
| WO | 2017154017 A1 | 9/2017 |
| WO | 2018069833 A1 | 4/2018 |
| ZA | 8400670 | 9/1985 |

OTHER PUBLICATIONS

Wang Y. et al.; Crystal Structures and Spectroscopic Properties of Zinc(II) Ternary Complexes of Vitamin L, H ý and Their Isomer /«-Aminobenzoic Acid with Bipyridine; Chem. Pharm. Bull; 53(6):645-652, 2005.

Wells, Structural Inorganic Chemistry, p. 572 (3d ed. 1962).

Wikipedia entry "Sacubitril" (in German), downloaded Apr. 14, 2021.

(56) References Cited

OTHER PUBLICATIONS

Wikipedia entry "Van der Waals force", retrieved from "https://en.wikipedia.org/w/index.php?title=Van_der_Walls_force&oldid=1012426507", last edit date Mar. 16, 2021.
Williford, Sharma et al, "Spatial Heterogeneity of Intracellular Ca concentration in nonbeating guinea pig ventricular myocytes", Circ Res, 1990, vol. 66, No. 1, pp. 241-248.
Wood et al., "Structure-based design of aliskiren, a novel orally effective renin inhibitor" Biochemical and Biophysical Research Communications, 2003, vol. 308, pp. 698-705.
Xu, textbook portion "Pharmaceutical Chemistry", 1996.
Yamada et al, CAPLUS Abstract AN 1995:4126620, Aug. 23, 1994.
Yung, S. L., "Hydrothermal Crystallization of Organic Compounds", Thesis, the Hong Kong University of Science and Technology, 2004.
Zaitu, et al. "A 2:1 Molecular Complex of Theophylline and 5-Fluorouracil as the Monohydrate", Acta Crystallogr. C: Struct. Chem., 51 (1995), pp. 1857-1859.
Zannad, "The Emerging Role of ACE inhibitors in the treatment of disease", Journal of Cardiovasc. Pharmacol., 1990, vol. 15, Suppl. 2, pp. S1-S5.
Zhang et al., "Technology and Principle for Manufacture of Tablets", Chinese Textbook with English translation, 1991.
Zhang, "Use of Coloring Agent in Pharmaceutical Formulation", Tianjing Pharmacy, 8(4):36-38. 1996.
Zhang, W., et al., "A Simplified Table for Conversion Between 2-theta Value and d Value in X-Ray Powder Diffraction Pattern", Journal of Ningxia University (Natural Science Edition), 2007.
Zhou, Academic Dissertation for Master Degree, "Theoretical Study of Intermolecular Interaction Between Tetrazole Compounds and Dimers of Tetrazole and Water", Ch. II, 2005.
Zumdahl et al., Chemistry 68-110 (1oth ed. 2018).
De-Dong W. et al.; Formation of Various Polymeric Frameworks by Dicarboxylate-Like Ligands: Synthesis and Crystal Structures of Polymeric Complexes of Sodium Perchlorate with Flexible Double Betaines. Structural Chemistry, vol. 7, No. 2, 1996.
Defendants' Joint Initial Invalidity Contentions Under Local Patent Rules; Action regarding U.S. Pat. Nos. 8,877,938 and 9,388,134; Dec. 4, 2020.
Definition of "Supramolecular assembly" https//en.wikipedia.org/wiki/Supramolecular_assembly, downloaded Oct. 22, 2019.
Desiraju, "Chemistry beyond the molecule", Nature, 412(6845):397-400, 2001.
Diovan (valsartan) Patient Information 2004.
Diovan (valsartan) Prescribing Information 2002.
Drug Design, (ed. Qiu Zhuibai), Higher Education Press, Edition 1, p. 105. 1999.
Drug Design, Chapter 2—Principles and Methods of Drug Design, edited by Qiu Zhuibai, High Education Press, Edition 1, pp. 223-226, Dec. 1999.
Duniz, et al, Exercises in prognostication: Crystal structures and protein folding, PNAS, 2004, vol. 101, vol. 101, No. 40, pp. 14309-14311.
EMA Note for Guidance on Pharmaceutical Development (May 2006).
EMEA (European Medicines Agency) Specifications: Test Procedures and Aceeptance Criteria for New Drug Substances and New Drug Products: Chemical Substances, May 2000.
Encyclopedia Britannica entry "Van der Waals force", retrieved from https://www.britannica.com/science/van-der-Waals-forces, access date Apr. 13, 2021.
English-Chinese Dictionary of Chemistry and Chemical Engineering (4th Edition), 2000.
Entresto Label, Nov. 24, 2015.
Entresto Prescribing Information, Aug. 2015.
Erdos, "Angiotensis I converting enzyme and the changes in our concepts through the years", Lewis K. Dahl Memorial Lecture, Hypertension, 1990, vol. 16, No. 4, pp. 363-370.
Etter, "Hydrogen Bonds as Design Elements in Organic Chemistry", J. Phys. Chem., 95:4601-4610, 1991.

Etter, M.C., et al, "Hydrogen-Bond Directed Cocrystallization as a Tool for Designing Acentric Organic Solids", Chemistry of Materials, 1(1):10-12, 1989.
European Medicines Agency, Guidelines by the European Medicines Agency of May 2000, "ICH Topic Q6A-Specifications: Test Procedures and Acceptance Criteria for New Drug Substances and New Drug Products: Chemical Substances", 2000.
Examiner's reservation of Aug. 17, 2015 in the scope of Examination of divisional application 219782.
FDA Chemical Review NDA 207620—In the registration file of the composition valsartan/sacubitril (trade name Entresto) it is mentioned (p. 95). 2015.
FDA Co-Crystal Directives of 2013: Guidance for Industry: Regulatory Classifcation of Pharmaceutical Co-Crystals. 2013.
Feng et al. "LCZ696: a dual-acting sodium supramolecular complex"; 2012; Tetrahedron Letters 53:275-276.
Feng, et al., "High-throughput crystallization in pharmaceutical research and development", Acta Pharmaceutica Sinica, 40(6):481-485. 2005.
Fields, Larry E. et. al, The Burden of Adult Hypertension in the United States 1999 to 2000. A Rising Tide. Hypertension. 2004; 44:398-404.
French and Morrison, Identification of Complexes of Phenobarbital with Quinine, Quinidine, or Hydroquinidine in Pharmaceutical Dosage Forms, J Pharm Sci, 54(8):1133-1136, 1965.
Fujioka and Tan, "Biopharmaceutical Studies on Hydantoin Derivatives. III. Physio-Chemical Properties, Dissolution Behavior, and Bioavailability of the Molecular Compound of 1-Benzenesulfonyl-5,5-Diphenylhydantoin and Anti-Pyrine", J Pharm Dyn, 5:475-484, 1982.
Gardner, "Drugs as Materials: Valuing Physical Form in Drug Discovery" 2004; Nature Reviews, vol. 3: 926-934.
General Chemistry, Ch. 3: "Substance Structure and Periodic law of Elements", Sec. 7: Intermolecular force and hydrogen bond, edited by Tianpeng Cao, 2000.
German Supreme Court, GRUR, 2012 [English Translation].
Griesser, "The Importance of Solvates", Polymorphism in the Pharmaceutical Industry, (Ed. Rolf Hilfiker) Ch. 8, p. 211-233. 2006.
"Gu. J., et al., ""Pharmacokinetics and Pharmacodynamics of LCZ696, a Novel Dual-Acting AngiotensinReceptor-Neprilysin Inhibitor (ARNi)"",The Journal of Clinical Pharmacology, 50:401-414,2010.".
Guillory et al, Chapter 7, pp. 183-226 of "Polymorphism in Pharmaceutical Solids", 1999, vol. 95.
Guillory et al., "Interactions Between Pharmaceutical Compounds by Thermal Methods", J Pharm Sci, 58(3):301-308, 1969.
Guillory, "Generation of Polymorphs, Hydrates, Solvates, and Amorphous Solids", Polymorphism in Pharmaceutical Solids (ed. Harry G. Brittain), vol. 95, Chapter 5, pp. 183-226. 1999.
Haleblian, et al. "Characterization of Habits and Crystalline Modifications of Solids and Their Pharmaceutical Applications", J_ Pharm. Sci., 64, 8, 1269-1288 (1975).
Haleblian, et al. "Pharmaceutical Applications of Polymorphism", 58 J. Pharm. Sci., 911-929 (1969).
Hickey, et al., "Performance comparison of a co-crystal of carbamazepine with marketed product", European Journal of Pharmaceutics and Biopharmaceutics, 67:112-119. 2007.
Hoffman, D., "Is Novartis' LCZ696 "revolutionary" or just a marginal improvement?", Philly.com. 2014 (downloaded Dec. 11, 2015).
Hsieh et al., "Non-Isothermal Dehydration Kinetic Study of Aspartame Hemihydrate using DSC, TGA, and DSC-FTIR Microspectroscopy", Asian J_ Pharm. Sci., 13, 212-219 (2018).
Hughes D.L. et al; Crystal Structures of Complexes between Alkali-metal Salts and Cyclic Polyethers. Part IX.t Complex formed between Dibenzo-24-crown-8 (6,7,9,10,12,13,20,21,23,24,26,27-Dodecahydrodibenzo[b,n][1,4,7,10,13,16,19,22]octaoxacyclotetracosin) and two molecules of Sodium IMitrophenolate. J. Chem. Soc., Dalton Trans., 2374-2378, Jan. 1, 1975.
ICH Harmonized Tripartite Guideline, Good Manufacturing Practice Guide for Active Pharmaceutical Ingredients, 2000.

(56) References Cited

OTHER PUBLICATIONS

Intengan et al, "Resistance Artery mechanics, structure, and Extracellular Components in Spontaneously Hypertensive Rats", Circulation, Nov. 30, 1999, pp. 2267-2275.
Intengan, Thibault, Li et al, "Blood Pressure and Small Arteries in DOCA-salt-treated genetically AVP-deficient rats", Hypertension, 1999, vol. 34, No. 4, Part 2, pp. 907-913.
Interim Development Report, Feb. 23, 2017.
Israili, "Clinical pharmacokinetics of angiotensin II (AT 1) receptor blockers in hypertension", Journal of Human Hypertension, 14, Suppl 1, S73-S86. 2000.
IUPAC nomenclature of organic chemistry from Wikipedia, downloaded Apr. 10, 2017.
Izzo, Jr., et al., "Efficacy and Safety of Crystalline Valsartan/Sacubitril (LCZ696) Compared With Placebo and Combinations of Free Valsartan and Sacubitril in Patients With Systolic Hypertension: The RATIO Study", J. Cardiovasc. Pharmacol. 69(6):374-381, 2017.
Jiuzhou Pharmaceutical: the sale of Entresto is slower than expected, and an extended layout is expected in a short term, Guang Fa Securities, Tencent News. 2016.
Joint Claim Construction Brief and Appendices; Action regarding U.S. Pat. Nos. 8,877,938; and 9,388,134; May 21, 2021.
Randy Webb Declaration, signed May 11, 2006 (Filed in U.S. Appl. No. 10/341,868).
Registration file of the composition valsartan/sacubitril (trade name Entresto)—p. 4 of the Summary Review document, 2015.
Regulatory Classification of Pharmaceutical Co-Crystals Guidance for Industry, 2018, p. 3.
Remenar, et al. "Crystal Engineering of Novel Cocrystals of a Triazole Drug with 1,4-Dicarboxylic Acids" J. Am. Chem. Soc. 125:8456-8457, 2003.
Remenar, et al., "Salt Selection and Simultaneous Polymorphism Assessment via High-Throughput Crystallization: The Case of Sertraline", Organic Process Research & Development, 7:990-996, 2003.
Remington: The Science and Practice of Pharmacy, 21st Edition, 2005, pp. 730-740, 900, 924, 929, 1035-1036.
Reply to Communication pursuant to Art 94(3) dated Mar. 25, 2013 regarding European Patent Application No. 10176094.0 submitted Oct. 3, 2013.
Reports on the filing or determination of an action regarding a patent; File history of U.S. Pat. No. 8,877,938; Jun. 29, 2020-Mar. 31, 2021.
Reports on the filing or determination of an action regarding a patent; File history of U.S. Pat. No. 9,388,134; Jun. 29, 2020-Mar. 31, 2021.
Response to the communication under Article 94(3) EPC dated Oct. 3, 2013 in EP Patent Application No. 10176094.0.
Rifaximin alpha decision by the federal Supreme Court (BGH), GRUR 2019, 157. English translation.
Rissanen K. et al; Self-assembly by co-ordination and strong hydrogen bonding. X-ray crystal structures of a dimeric trisodium complex of a new acidic complexing ligand and its dehydrate. Supramolecular Chemistry. 247-250, 1991.
Rodriguez-Spong, et al., "General principles of pharmaceutical solid polymorphism: a supramolecular perspective", Advanced Drug Delivery Reviews, 56(3):241-274. 2004.
Roques, Bernard P. et.al, Neutral endopeptidase 24.11: Structure, Inhibition, and Experimental and Clinical Pharmacology, Pharmacological Reviews, vol. 45, No. 1, pp. 87-146, 1993.
Rose, Erythromycin and Some of Its Derivatives, Analytical Chemistry, 26, 5, 938-939 (1954).
Rubattu, Speranza, et.al, "The atrial natriuretic peptide: a changing view." Journal of Hypertension, 2001, vol. 19, No. 11, pp. 1923-1931.
Ruilope, Luis M, et al, "Blood-pressure reduction with LCZ696, a novel dual-acting inhibitor of the angiotensin II receptor and neprilysin" Lancet 2010; 375:1255-66.
Sangster, "Phase Diagrams and Thermodynamic Properties of Binary Systems of Drugs", J Phys Chem Ref Data, 28(4):889-930, 1999.
Sardone et al., "Trimethoprin-Sulfadimidine 1:21 Molecular Complex Monohydrate", Acta Cryst, C53, pp. 1295-1299, 1997.
Schartman, R.R., "On the thermodynamics of cocrystal formation", International Journal of Pharmaceutics, 365:77-80. 2009.
Sekiguchi and Ito, "Studies on the Molecular Compounts of Organic Medicinals. I. Dissolution Behavior of the Molecular Compound of Sulfanilamide and Sulfathiazole", Chem Pharm Bull 13(4):405-413, 1965.
Shefter E. et al.; Structural Studies on Molecular Complexes V: Crystal Structures of Sulfathiazole-Sulfanilamide and Sulfathiazole-Theophylline Complexes. Journal of Pharmaceutical Sciences. vol. 60(2): 282-286, Feb. 2, 1971.
Shimizu and Nishigaki, Structure of 2,4-Diamino-5-(3,4,5-trimethoxybenzyl)pyrimidine-5,5-Diethylbarbituric Acid (1:1), Acta Cryst., B38:2309-2311, 1982.
Shou 2006 Chemical Engineer: Shou Kaisheng, Cultivation of singe crystal for X-ray diffraction test, Chemical Engineer, No. 4, Apr. 2006, pp. 64-66.
Sokolov et al, "Synthesis and the crystal structure of the supramolecular complex [Cl3InW3S4(H2O)9]2+ with cucurbituril", Russian Chemical Bulletin, International Edition, vol. 50, No. 7, p. 1144-1147, (2001).
Sonnenberg, J.L. et. al, "Identification of Protease 3.4.24.11 as the Major Atrial Natriuretic Factor Degrading Enzyme in the Rat Kidney," Peptides, vol. 9, pp. 173-180, May 29, 1987.
Stahl, Heinrich et al., Helvetica Chimica Acta,"Handbook of Pharmaceutical Salts . . . " 2002, pp. 265-327.
Stahly, G. Patrick, "A Survey of Cocrystals Reported Prior to 2000" Crystal Growth and Design Perspective, 2009, vol. 9, pp. 4212-4229.
State Food and Drug Administration (SFDA), 2006 National Drug Standard, vol. 49, edited by National Pharmacopoeia Committee.
Stephenson and Kenny, "Metabolism of Neuropeptides", Biochem. Journal, 1987, vol. 241, pp. 237-247.
Stephenson et al, "The hydrolysis of a human atrial natriuretic peptide by pig kidney microvillar membranes is initiated by endopeptidase-24.11", Biochem J., 1987, vol. 243, pp. 183-187.
Stout, G.H. et al., "X-ray Structure Determination, A Practical Guide, Symmetry Operations and Space Groups", 1968, Chpt. 3.
Sugano et al, CAPLUS Abstract AN 1995:931230; JP 07157459, Jun. 29, 1995.
Sybertz et al, "Atrial natriuretic factor-potentiating and antihypertensive activity of SCH 34826", Hypertension, 1990, vol. 15, No. 2, pp. 152-161.
Sybertz et al, "SCH 39370, a neutral metalloendopeptidase inhibitor, potentiates biological responses to atrial natriuretic factor and lowers blood pressure in desoxycorticosterone acetate-sodium hypertensive rats", J Pharmacol. Exp. Ther., 1989, vol. 250, No. 2, pp. 624-631.
Takasu, K, et. al, "Synthesis ad Evaluation Carbolinium Cations as New Antimalarial Agents based on Delocalized Lipophilic Cation (DLC) Hypothesis", Chem. Pharm. Bull. 53(6) 653-661 (Jun. 2005).
Taub et al, CAPLUS Abstract AN 1986:573042, ZA 8400670, Sep. 25, 1985.
Technical Guidelines for Research on Bioavailability and Bioequivalence of Chemical Drug Formulations, (Guidelines No. [H]GCL2-1), issued by CFDA, 2005.
Testimony of Prof. Dahloff, Mar. 4, 2015 (English Translation).
The American Heritage Dictionary of the English Language, 3rd Ed., p. 1792, 1992.
The Merck Index entry for Entresto®, downloaded Aug. 23, 2017.
Third party observation, Opposition against EP1948158B (EP06827689. 8), Feb. 19, 2016.
Trapani, Angelo J., et. al, "CGS 35601 and its orally Active Prodrug CGS 37808 as Triple Inhibitors of Endothelin-converting Enzyme-1, Neutral Endopeptidase 24.11, and Angiotensin-converting Enzyme." J Cardiovasc Pharmacol, vol. 44, Supplement 1, Nov. 2004, S211-S215.
US FDA Entresto Prescribing Information, 2015.

(56) References Cited

OTHER PUBLICATIONS

Variankaval, et al., "Preparation and Solid-State Characterization of Nonstoichiometric Cocrystals of a Phosphodiesterase-IV Inhibitor and L-Tartaric Acid", Crystal Growth & Design, 6(3):690-700. 2005.
Vippagunta et al., "Crystalline solids", Advanced Drug Delivery Reviews, 48:3-26. 2001.
Vishweshwar, Peddy et al., "Crystal engineering of pharmaceutical co-crystals from Polymorphic active pharmaceutical Ingredients", Chem. Communication, pp. 4601-4603, 2005.
Vishweshwar, Peddy, Journal of Pharmaceutical Sciences, vol. 95, No. 3, Mar. 2006; Review: Pharmaceutical Co-Crystals, (Univ of South Florida), pp. 499-516.
Vogt, et al., "A Study of variable hydration states in topotecan hydrochloride", Journal of Pharmaceutical and Biomedical Analysis, 40:1080-1088. 2006.
Vranic, "Amorphous Pharmaceutical Solids", Bosnian Journal of Basic Medical Sciences, 4(3):35-39. 2004.
Kaneniwa & Otsuka, "The Interaction between Water and Cephalexin in the Crystalline and Noncrystalline States," Chem. Parm. Bull. 32(11): 4551-4559 (1984).
Kario, K., et al., "Efficacy and Safety of LCZ696, a First-in-Class Angiotensin Receptor Neprilysin Inhibitor, in Asian Patients with Hypertension, A Randomized, Double-Blind, Placebo-Controlled Study", Hypertension, 63:698-705, 2014.
Kawashima, Y., et al., "Preparation of directly compressible powders of a physical mixture and a complex of throphylline-phenobarbital using spray-drying", International Journal of Pharmaceutics, 18:345-343, 1984.
Kearney, Patricia M., et. al, "Global burden of hypertension: analysis of worldwide data" Lancet, 365: 217-223, 2005.
Khankari et al., "Pharmaceutical hydrates", Thermochimica Acta, 248, 61-79 (1995).
King, J. B., et al., "Neprilysin Inhibition in Heart Failure with Reduced Ejection Fraction: A Clinical Review", Pharmacotherapy, 35(9):823-837, 2015.
Ksander et al., Journal of Medicinal Chemistry, vol. 38, No. 10, 1995, pp. 1689-1700.
Lachman, Lieberman and Kanig, The Theory and Practice of Industrial Pharmacy, 1986, p. 330-331, 3rd edition.
Latif et al., Drug Development and Industrial Pharmacy, 2018 vol. 44, No. 7, 1099-1108.
Levy, et al., "The Progression From Hypertension to Congestive Heart Failure", JAMA, 275(20):1557-1562, 1996.
Liang Wenquan, "Polymorph", Biopharmaceuticals and pharmacokinetics, 2002.
Liu, X. J., et al., "Study on Co-Crystallization of LCZ696 Using In Situ ATR-FTIR and Imaging" Crystals, 10, 922, 1-18, 2020.
Luft, et al., "Macromolecular crystallization in a high throughput laboratory—the search phase", Journal of Crystal Growth, 232:591-595, 2001.
Martin, et al., "Polyphenol-Caffeine Complexation", J. Chem. Soc., Chem. Commun. 2:105-106. 1986.
Matsumoto et al, "Blockade of rennin-angiotensin system and enhancement of atrial natriuretic peptide with neutral endopeptidase inhibition cause natriuresis in congestive heart failure and renal dysfunction in conscious dogs", Abstract, JASN, Hemodynamics and Vascular Regulation, Sep. 1993, pp. 517.
McMurray et al.; Angiotensin-Neprilysin Inhibition versus Enalapril in Heart Failure; 2014; New England Journal of Medicine; vol. 371, No. 1, pp. 993-1004.
Medicinal Chemistry 2nd Edition Edited by Zongru Guo China Medicinal Science and Technology Publishing House Published in Aug. 2003.
Medpage Today 5 Game-Changers in Cardiology in 2015: Entresto, 2015.
Miroshnyk, et al., "Pharmaceutical co-crystals—an opportunity for drug product enhancement", Expert Opin. Drug. Deliv. 6(4):333-341, 2009.
Morissette et al.; "High-throughput crystallization: ploymorphs, salts, co-crystals and solvates of pharmaceutical solids"; 2004; Advanced Drug delivery Reviews; 56: 275-300.
Morissette, et al., "Elucidation of crystal form diversity of the HIV protease inhibitor ritonavir by high-throughput crystallization", PNAS, 100(5):2180-2184, 2003.
Morris and Rodriguez-Hornedo, "Hydrates", Encyclopedia of Pharmaceutical Technology, 7:393-440. 1993.
Morris et al., "An integrated approach to the selection of opitmal salt form for a new drug candidate", Int. J. Pharm. 105 (1994) 209-217.
Nakai H. et al.; X-Ray and Infrared Spectral Studies of the Ionic Structure of Trimethoprim t-Sulfamethoxazolet1 :1 Molecular Complex. J. Chem. Soc. Perkin Trans; 1459-1464, 1984.
Nakao et al: "The Crystal and Molecular Structure of the 2:1 Molecular Complex of Theophylline with Phenobarbital", Acta Cryst., 1977, B33, pp. 1378-1384.
Nakao, et al. "The crystal and molecular structure of the 2: 1 molecular complex of theophylline with phenobarbital", Acta Crystallogr_ B, 33 (1977), pp. 1373-1378.
Needleman et al, "The biochemical pharmacology of atrial peptides", Annual Review Pharm., Tox., 1989, vol. 29, pp. 23-41.
Novartis' letter of Feb. 11, 2013 to the European Patent authority.
Novartis Notice of Marketing of Entresto, Summary of Product Characteristics, Ministry of Health, Nov. 2015 (English Translation).
Novartis Response to A94(3), Jan. 4, 2018 in EP Patent Application No. 10176094.0.
Novartis Response to A94(3), Jan. 7, 2010 in EP Patent Application No. 06827689.8.
Online dictionary (Merriam-Webster) for the definition of "subtherapeutic", downloaded 2019.
Organic Chemistry Experimentation, 2.3, Recrystallization and Filtration, Edited by Guanggen XI, Changhong Zhao, Zhongde Zhao, et al., Published by East China University of Science and Technology Press, 1st edition, 1st printing, pp. 31-37, 1995.
Otsuka and Kaneniwa, "Hygroscopicity and Solubility of Noncrystalline Cephalexin", Chem. Pharm. Bull. 31(1) p. 230-236 (1983).
Packer, M., et al., "Comparison of Omapatrilat and Enalapril in Patients With Chronic Heart Failure", Circulation, 920-926, 2002.
Papadimitriou C. et al.; Chloranilate bridged sodium chains. Inorganic Chemistry Communications 1; 418-420, 1998.
Patel, Mona et.al, "Treatment of non-insulin-dependent diabetes mellitus", Expert Opin. Investig. Drugs (2003) 12(4):623-633.
Patentee's submission of Feb. 11, 2013, in EP 06 827 689.8.
Petition for Patent Term Extension—IL Patent Application No. 184027 (under opposition) and IL Patent Registration No. 162661, Feb. 17, 2016 (English Translation).
"Pharmaceutical Chemistry (a training textbook for qualification exam of licensed pharmacist), edited by Mingxia Xu, Published by China Medical Science and Technology Press, 1st edition, 2nd printing, Chapter 19, Section 2, p. 221,1988."
"Pharmaceutics, edited by Chuanfu Yu, Published by People's Medical Publishing House, 1st edition, 1st printing, Chapter 15: ""Introductions for other formulations"", Section 6: ""Prodrug Formulation"", pp. 417-419, 1986."
Physical Pharmaceutics, (ed. Desen Su and Siling Wang), Chemical Industry Press, Edition 1, p. 9 and 17. 2004.
Polymorphic Drugs, Ed. Yang Lu & Guanhua Du, People Health Publishing House, First Edition, Ch. II, 2009.
Polymorphism in Molecular Crystals, Joel Bernstein, Clarendon Press/Oxford, Oxford (UK), pp. 27,46-49, 112, 150 and 151, (2002).
Polymorphism in Pharmaceutical Solids in Drugs and the Pharmaceutical Sciences 1999, vol. 95 (edited by H. G. Brittain, Marcel Dekker, Inc) pp. 197-199 "crystallization from melt".
Polymorphism in Pharmaceutical Solids in Drugs and the Pharmaceutical Sciences, vol. 95 (edited by H. G. Brittain), Marcel Dekker, Inc, pp. 229-278, (1999).
Preparation called Diovan and Co-Diovan in free base form, 2003.
Prescribing Information for Entresto (sacubitril and valsartan), for oral use, revised Feb. 2021.
Prescribing Information for Entresto (sacubitril and valsartan), for oral use, revised Oct. 2019.

(56) References Cited

OTHER PUBLICATIONS

Principle of IUPAC Nomenclature of Organic Compounds, Zhejiang Science & Technology Publishing house 1985.
"Chemical and Pharmaceutical Bulletin," Instructions to Authors (last updated Jan. 1, 2020).
"Drug Structures and Formulations" edited by Jianmin Shen and Zhenqing Wu, Aug. 1989, preface, contents, and p. 104.
"Guideline on clinical investigation of medicinal products in the treatment of hypertension", European Medicines Agency, Science Medicines Health, EMA/238/1195/Rev. 3, p. 1-18, 2010.
"Handbook of Pharmaceutical Salts Properties, Selection, and Use", Ed. Stahl and Wermuth, forward, preface, contents and p. 214. 2002.
"Principle of Nomenclature of Organic Compounds", Science Publishing House, pp. 146 and 268, 2017.
"The Practice of Medicinal Chemistry" edited by Camille Georges Wermuth et.al. and translated by Yumin Chi, Apr. 2005, preface, contents, and p. 822.
Aakeroy, C. B., et al., "Cocrystal or Salt: Does It Really Matter?", Molecular Pharmaceutics, 4(3):317-322, 2007.
Aakeroy, C.B., et al., "Avoiding 'Synthon Crossover' in Crystal Engineering with Halogen Bonds and Hydrogen Bonds", Crystal Growth and Design, 11:5333-5336, 2011.
Aakeroy, C.B., et al., "Building co-crystals with molecular sense and supramolecular sensibility", Cryst. Eng. Comm., 7(72):439-448, 2005.
Aakeröy,Christer et.al.; "Crystal Engineering: Strategies and Architectures", Acta Crystallographica Section B, pp. 569-586; ISSN 0108-7681 1997.
Affidavit of Alan Graff; Dated Feb. 17, 2016.
Aitipamula, S., et al., "Polymorphs, Salts, and Cocrystals: What's in a Name?", Crystal Growth & Design, 12:2147-2152, 2012.
Almarsson Organic Crystal Engineering: Frontiers in Crystal Engineering, Edited by Tiekink, E.R.T., Vital, J., and Zaworotko, M., John Wiley and Sons. pp. 69-70,87-90 and 98, 2010.
Almarsson, Oern et al., Chem. Community, 2004, pp. 1889-1896.
Almeida et al, "Clearance Function of Type C receptors of Atrial Natriuretic Factor in rats", American Journal of Physiology, 1999, vol. 256, pp. R469-R475.
Andrews P.C.et al.; Synthesis and Crystal Structures of [C6H4SC(-S)-NNa—3P(NMe2)3O.NAN-(S-)CSC6H4] and [C6H4SC(~S}~NLipmdien] (pmdien = N,N,N',N'',N''',N'''-Pentamethyldiethylenetriamine): Alkali-metal Amides from 2-Sulfanyfbenzothiazole. J. Chem. Soc. Dalton Trans. 4059-4065,1995.
Applicant's submissions pursuant to rule 116 EPC of Feb. 11, 2013 in EP Patent Application 06827689.8.
Armstrong, "A Review of High-Throughput Screening Approaches for Drug Discovery", 1999; Am. Biochem. Lab., p. 26-28.
Basic Material Science, Part II: "Basic Theory of Material Structure", Ch. 3: "Atomic structure and bonding", edited by Zhangzhong Wang, 2015.
Basic Medical Chemistry, Ch. 8: "Molecular Science", Sec. 3: "Intermolecular force", edited by Zhao, Q and Liu, L, Ed., 2015.
Bazil K et al, "Telemetric monitoring of cardiovascular parameters in conscious spontaneously hypertensive rats", Journal of Cardiovascular Pharmacology, 1993, vol. 22, pp. 897-905.
Berge, Stephen M. et al., Pharmaceutical Salts, Journal of Pharmaceutical Sciences, vol. 66 (1), pp. 1-19, 1977.
Bettinetti and Giordano, "Interaction Between Trimethoprim and Some Sulfa Drugs", Drug Development and Industrial Pharmacy, 14(4):431-449. 1988.
Bettinetti et al., "Structure and Solid-State Chemistry of Anhydrous and Hydrated Crystal Forms of the Trimethoprim-Sulfamethoxypyridazine 1:1 Molecular Complex", Journal of Pharmaceutical Sciences, 89(4):478-489. 1999.
Bettinetti, et al. "Methanol solvate of the 1: 1 molecular complex of trimethoprim and sulfadimidine", Acta Crystallogr. C: Struct. Chem, 53 (1997), pp. 594-597.
Biopharmaceutics and Pharmacokinetics, Ch. 11 "Nonlinear Pharmacokinetics", Section One, (2000).

Black et al., "Valsartan, a new angiotensin II antagonist for the treatment of essential hypertension: efficacy, tolerability and safety compared to an angiotensin-converting enzyme inhibitor, lisinopril", Journal of Human Hypertension, 1997, vol. 11, pp. 483-489.
Bohlender, J., et al., "High Human Renin Hypertension in Transgenic Rats", Hypertension, vol. 29, No. 1, Part 2, Jan. 1997, pp. 428-434.
Braga, D., et al., "From unexpected reactions to a new family of ionic co-crystals: the case of barbituric acid with alkali bromides and caesium iodide", Chem. Comm. 46:7715-7717, 2010.
Brittain and Byrn, "Structural Aspects of Polymorphism", Polymorphism in Pharmaceutical Solids (ed. Harry G. Brittain), vol. 95, Chapter 3, pp. 74-124. 1999.
Brittain, Methods for the Characterization Polymorphism in Pharmaceutical Solids 1999 pp. 227-278.
Byrn et al., "Solid-state Pharmaceutical Chemistry", Chem. Mater., 6, 1148-1158 (1994).
Byrn et al., Solid State Chemistry of Drugs (2d ed. 1999), pp. 47-58.
Byrn, Stephen et al., "Pharmaceutical Solids: A Strategic Approach to Regulatory Considerations", Pharmaceutical Research, vol. 12 (7), pp. 945-954, 1995.
Caira, "Molecular complexes of sulfonamides. 2. 1:1 complexes between drug molecules: sulfasimidine-acetylsalicyclic acis and sulfadimidine-4-aminosalicyclic acid", J Crystallogr Spectrosc Res, 72(2):193-200, 1992.
Carter, et al., "Hydrochlorothiazide Versus Chlorthalidone Evidence Supporting Their Interchangeability", Hypertension, 43:4-9, 2004.
Chen 2003 Science Press : Principle and Practice of Single Crystal Structure Analysis, edited by Chen Xiaoming and Cai Jiwen, 2003, Science Press, cover page, copyright page, Table of Contents, pp. 2, 41-44, 126-127.
Childs S. L. et al.; Crystal Engineering Approach to Forming Cocrystals of Amine Hydrochlorides with Organic Acids. Molecular Complexes of Fluoxetine Hydrochloride with Benzoic, Succinic, and Fumarie Acids. JACS Articles; vol. 126: 13335-13342, Apr. 1, 2004.
Chinese Pharmacopoeia, Part IV, 0451: X-ray diffraction method, Edited by National Pharmacopoeia Committee, Chinese Medical Science Press, 2015.
Cody, Robert J. et al., "Physiologic and Pharmacologic Studies of Atrial Natriuretic Factor: Anatriuretic and Vasoactive Peptide", Therapeutic Review, J Clin Phrmacol 1987, 27:927-936.
Compiled references relating to the compounds listed in Annex 2 named using "butylcarbamoyl" or "carbamoylpropionate" nomenclature, 2017.
Concise Course of Social Chemistry, edited by Pingchu Chen, Wuke Li, Zhengkun Zhan, Published by Higher Education Press, 1st edition, 1st printing, Chapter 2: "Chemistry in modern society", Section 2.5.2: "Supermolecular Chemistry", pp. 64-66, 2004.
Consensus Trial Study Group, "Effects of enalapril on mortality in severe congestive heart failure", New England Journal of Medicine, 1987, vol. 316, No. 23, pp. 1429-1435.
"CPS 2004 ""Compendium of Pharmaceuticals and Specialities: The Canadian Drug Reference for Health Professionals""", Canadian Pharmacists Association. (""CPS2004""), p. 627-629".
Dahlof, et al., "Prevention of cardiovascular events with an antihypertensive regimen of amlodipine adding perindopril as required versus atenol adding bendroflumethiazide as required, in the Anglo-Scandinavian Cardiac Outcomes Trial-Blood Pressure Lowering Arm (ASCOT-BPLA): a multicentre randomized controlled trial", Lancet, 366:895-906, 2005.
Data which Novartis submitted to the Examiner in letter dated May 14, 2012.
Datta Sharmistha et al., "Crystal Structures of Drugs: Advances in Determination, Prediction and Engineering", Nature Reviews, vol. 3, pp. 42-57, 2004.
Day, et al, Significant progress in predicting the crystal structures of small organic molecules—a report on the fourth blind test, Acta Cryst. B65, pp. 107-125 (2009).
Decision X ZR 126/09 of the German Supreme Court: Obvious to combine two active ingredients into one pharmaceutical preparation—leflunomide (GRUR 2012, 1130), German document with English translation. Jul. 24, 2012.

(56) References Cited

OTHER PUBLICATIONS

U.S. Appl. No. 11/772,360, Granted.
U.S. Appl. No. 14/311,788, Granted.
U.S. Appl. No. 15/187,872, Abandoned.
U.S. Appl. No. 16/006,252, Abandoned.
U.S. Appl. No. 16/502,811, Abandoned.
U.S. Appl. No. 16/502,821, Abandoned.
U.S. Appl. No. 16/579,581, Granted.
U.S. Appl. No. 16/579,591, Abandoned.
U.S. Appl. No. 17/395,305, Pending.
U.S. Appl. No. 17/738,565, Abandoned.
Declaration of V. R. Prathap, Jan. 31, 2023.
Kumar et al., A Review about Regulatory Status and Recent Patents of Pharmaceutical Co-Crystals, Advanced Pharmaceutical Bulletin, 2018, 355-363, 8(3).
Prathap, Interim Development Report, Feb. 23, 2017.
Thurmann et al., Influence of the Angiotensin II Antagonist Valsartan on Left Ventricular Hypertrophy in Patients With Essential Hypertension, Circulation, 1998, 2037-2042.
Ansel et al., Dosage Form Design: Phamaceutic and Formulation Considerations, Pharmaceutical Dosage Forms and Drug Delivery Systems, 1999, 60-141, 7th Ed., Chapter 3.
Bailey Walsh et al., Crystal engineering of the composition of pharmaceutical phases, Chem. Commun, 2003, 186-187.
Yu et al., Physical characterization of polymorphic drugs: an integrated characterization strategy, PSTT, Jun. 1998, 118-127, 1(3).
Blagden et al., Current directions in co-crystal growth. New Journal of Chemistry, Oct. 2008, 1645-1808, 32 (10).
Blagden et al., Pharmaceutical co-crystals—are we there yet?, CrystEngComm, 2014, 5753-5761, 16.
Borka et al., Crystal polymorphism of pharmaceuticals, Acta Pharm. Jugosl., 1990, 71-94, 40.
Caira, Crystalline Polymorphism of Organic Compounds, Topics in Current Chemistry, 1998, 164-208, 198.
Cases, Omapatrilat: Clinical Pharmacology, Drugs of Today, 2000, 817-828, 36(12).
Chau et al., Development of Thalidomide and Tis IMiD Derivatives, Angiogenesis an Integrative Approach Drom Science to Medicine, 2008, 387-394, Chapter 34.
Chen et al., Renal Response to Acute Neutral Endopeptidase Inhibition in Mild and Severe Experimental Heart Failure, Circulation, 1999, 2443-2448, 100.
Cleland et al., Lack of efficacy of neutral endopeptidase inhibitor ecadotril in heart failure, The Lancet, 1998, 1657-1658, 351.
Cohn et al., Effect of the Angiotensin Receptor Blocker Valsartan on Morbidity and Mortality in Heart Failure: the Valsartan Heart Failure Trial (Val-HeFT), Clinical Abstracts, J American Heart Association, 2000.
Yamamura et al., Physicochemical properties of amorphous salt of cimetidine and diflunisal system, International Journal of Pharmaceutics, 2002, 213-221, 241.
Criscione et al., Pharmacological profile of valsartan: a potent, orally active, nonpeptide antagonist of the angiotensin II AT1-receptor subtype, Br. J. Pharmacol., 1993, 761-771, 110.
Crystallization, 4th ed., J.W. Mullin (ed.) (2001) pp. 27-30.
Declaration of Piotr H. Karpinski, Sep. 7, 2010.
EMA—Note for Guidance on Impurities Testing: Impurities in New Drug Substances Oct. 2006.
FDA Guidance for Industry Q3B(R2) Impurities in New Drug Products, Jul. 2006.
FDA Guideline for submitting documentation for the manufacture of and controls for drug products, Feb. 1987.
Ferrario et al., Counterregulatory Actions of Angiotensein-(1-7), Hypertension, Sep. 1997, 535-541, 30(3).
Gomez-Monterrey et al., New Thiol Inhibitors of Neutral Endopeptidase EC 3.4.24.11: Synthesis and Enzyme Active-Site Recognition, Journal of Medicinal Chemistry, 1994, 1865-1873, 37(12).
Gu et al., Polymorph Screening: Influence of Solvents on the Rate of Solvent-Mediated Polymorphic Transformation, Journal of Pharmaceutical Sciences, Nov. 2001, 1878-1890, 90(11).
Haines, Thermogravimetry, Thermal Methods of Analysis, 1995, 22-62, Chapter 2.
Holan et al., Design of co-crystallization processes with regard to particle size distribution. Chemical Engineering Science, 2015, 36-43, 128.
Karimi-Jafari et al., Creating Cocrystals: A Review of Pharmaceutical Cocrystal Preparation Routes and Applications, Crystal Growth & Design, 2018, 6370-6387, 18.
Trippodo et al., Repression of Angiotensin II and Potentiation of Bradykinin Contribute to the Synergistic Effects of Dual Metalloprotease Inhibition in Heart Failure, the Journal of Pharmacology and Experimental Therapeutics, 1995, 619-627, 272(2).
Khilnani et al., Antihypertensive Therapy in the Next Millennium: "Treat Hypertensive, not Hypertension", Indian Journal of Cardiology, 2000, 25-34, 3.
Kudzin et al., Outline of CHN Elementary and CN Environmental Analysis, ACTA Universitatis Lodziensis Folia Chimica, 2004, 75-88, 13.
Lieberman et al., Crystal Properties and Polymorphism, Pharmaceutical Dosage Forms, 1989, 34-41, VIII.
Malacco et al., Comparison of Valsartan and Irbesartan in the Treatment of Mild to Moderate Hypertension: A Randomized, Open-Label, Crossover Study, Current Therapeutic Research, Nov. 2000, 789-797, 61(11).
Threlfall, Analysis of Organic Polymorphs a Review, Analyst, Oct. 1995, 2435-2460, 120.
Mazayev et al., Valsartan in heart failure patients previously untreated with an ACE inhibitor, International Journal of Cardiology, 1998, 239-246, 65.
McInnes, Clinical Advantage of Valsartan, Cardiology, 1999, 14-18, 91 (Suppl 1).
Neutel et al., Antihypertensive Efficacy of Omapatrilat, A Vasopeptidase Inhibitor, Compared with Lisinopril, AJH, Apr. 1999, 124A, D054, 12(4), Part 2.
Ngilirabanga et al., Pharmaceutical co-crystal: An alternative strategy for enhanced physiochemical properties and drug synergy, Nano Select, 2021, 512-526, 2.
Oparil et al., The Efficacy and Safety of Valsartan Compared with Placebo in the Treatment of Patients with Essential Hypertension, Clinical Therapeutics, 1996, 797-810, 18(5).
Pavia et al., Crystallization: Purification of Solids, Introduction to organiz Laboratory Techniques a contemporary approach, 1982, Chapter 3, 481-491, Second Edition.
Physicians' Desk Reference_1999_Diovan.
Physicians' Desk Reference_2000_Diovan.
Remenar et al., Crystal Engineering of Novel Cocrystals of a Triazole Drug with 1,4-Dicarboxylic Acids, J. Am. Chem. Soc., 2003, 8456-8457, 125.
Sagnella, Practical implications of current natriuretic peptide, Journal of the Renin-Angiotensin-Aldosterone System, Dec. 2000, 304-315, 1(4).
Sheikh et al., Scalable solution cocrystallization: case of carbamazepine-nicotinamide I, CrystEngComm, 2009, 501-509, 11.
Shetty et al., Differential Inhibition of the Prejunctional Actions of Angiotensin II in Rat Atria by Valsartan, Irbesartan, Eprosartan, and Losartan, the Journal of Pharmacology and Experimental Therapeutics, 2000, 179-186, 294(1).
Skolnik et al., Combination Antihyoertensive Drugs: Recommendations for Use, Clinical Pharmacology, 2000, 3049-3056, 61(10).
Barnes et al., A Review of the Applications of Thermal Methods Within the Pharmaceutical Industry, Journal of Thermal Analysis, 1993, 499-509, 40.
Duggirala et al., Physical Stability Enhancement and Pharmacokinetics of a Lithium Ionic Cocrystal with Glucose, Crystal Growth & Design, 2014, 6135-6142, 14.
Burnier et al., Angiotensin II receptor antagonists in hypertension, Kidney International, 1998, S-107-S-111, 5, Suppl. 68.

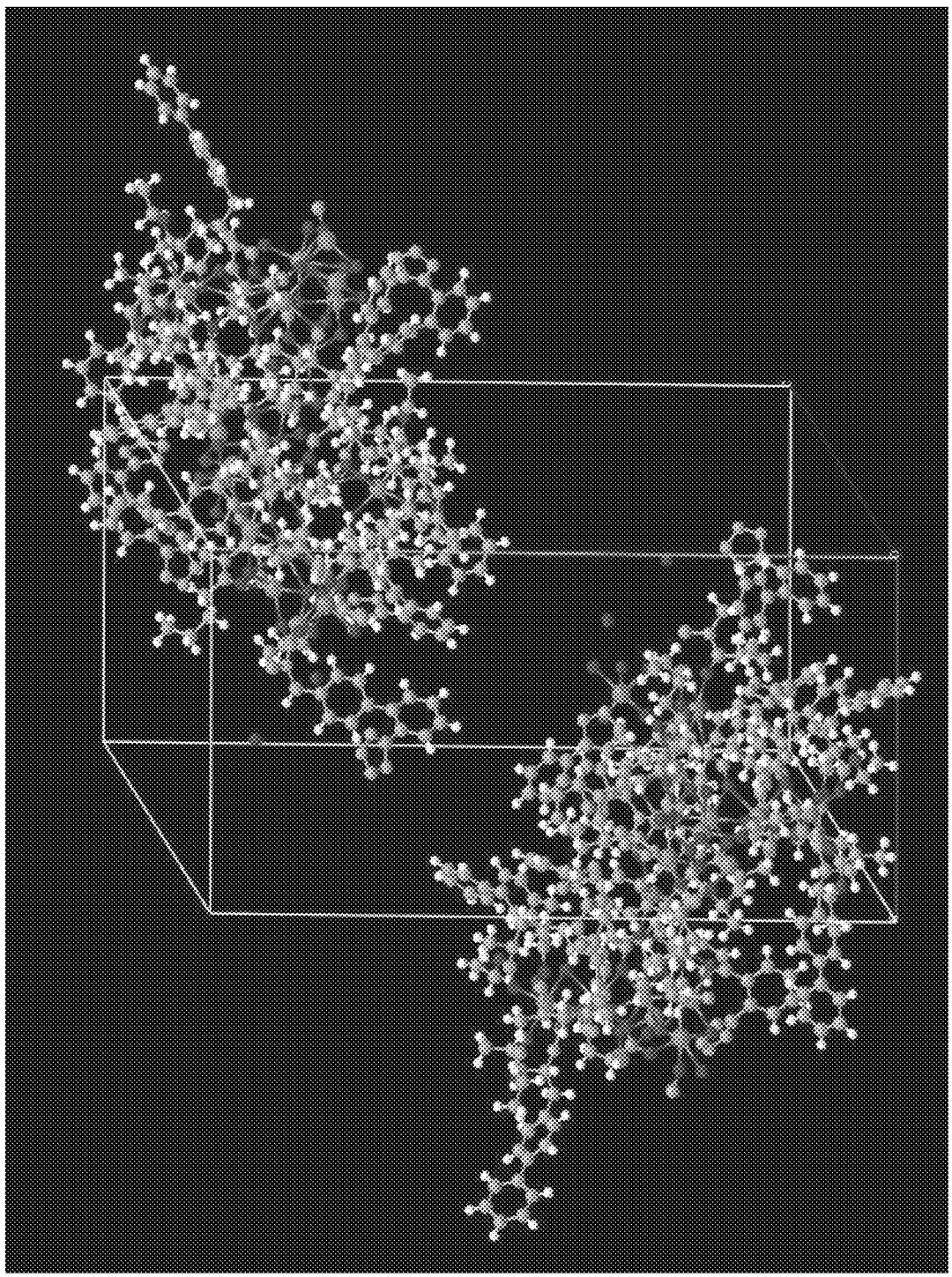

AMORPHOUS SOLID FORM OF COMPOUNDS CONTAINING S—N-VALERYL-N- {[2'-( 1 H-TETRAZOLE-5-YL)-BIPHENYL-4-YL]-METHYL}-VALINE AND (2R,4S)-5-BIPHENYL-4-YL-4-(3-CARBOXY-PROPIONYLAMINO)-2-METHYL-PENTANOIC ACID ETHYL ESTER MOIETIES AND SODIUM CATIONS

RELATED APPLICATIONS

This application is a continuation application of U.S. application Ser. No. 17/395,305, filed Aug. 5, 2021, which is a divisional application of U.S. application Ser. No. 16/579,581, filed Sep. 23, 2019, now U.S. Pat. No. 11,096,918, which is a continuation application of U.S. application Ser. No. 16/006,252, filed on Jun. 12, 2018, which is a continuation application of U.S. application Ser. No. 15/187,872, filed on Jun. 21, 2016, which is a divisional application of U.S. application Ser. No. 14/311,788, filed on Jun. 23, 2014, now U.S. Pat. No. 9,388,134, which is a divisional application of U.S. application Ser. No. 11/722,360, filed on Jan. 15, 2008, now U.S. Pat. No. 8,877,938, which is a national stage application, filed under 35 U.S.C. § 371, of International Application No. PCT/US06/43710, filed on Nov. 8, 2006, which claims the benefit of and priority to U.S. Provisional Application Nos. 60/822,086, filed Aug. 11, 2006, 60/789,332, filed Apr. 4, 2006, 60/735,541, filed on Nov. 10, 2005, and 60/735,093, filed on Nov. 9, 2005, the entire contents of each of which are incorporated herein by reference in their entireties.

FIELD OF THE INVENTION

The present invention is directed to dual-acting compounds and combinations of angiotensin receptor blockers and neutral endopeptidase inhibitors, in particular a dual acting molecule wherein the angiotensin receptor blocker and neutral endopeptidase inhibitor are linked via non-covalent bonding, or supramolecular complexes of angiotensin receptor blockers and neutral endopeptidase inhibitors, also described as linked pro-drugs, such as mixed salts or co-crystals, as well as to pharmaceutical combinations containing such a dual-acting compound or combination, methods of preparing such dual-acting compounds and methods of treating a subject with such a dual-acting compound or combination. Specifically, the invention is directed to a dual acting compound or supramolecular complex of two active agents having the same or different modes of action in one molecule.

BACKGROUND OF THE INVENTION

Angiotensin II is a hormone that causes blood vessels to constrict. This, in turn, can result in high blood pressure and strain on the heart. It is known that angiotensin II interacts with specific receptors on the surface of target cells. Two receptor subtypes for angiotensin II, namely AT1 and AT2, have been identified thus far. In recent times, great efforts have been made to identify substances that bind to the AT1 receptor. Angiotensin receptor blockers (ARBs, angiotensin II antagonists) are now known to prevent angiotensin II from binding to its receptors in the walls of blood vessels, thereby resulting in lower blood pressure. Because of the inhibition of the AT1 receptor, such antagonists can be used, therefore, as anti-hypertensives or for the treatment of congestive heart failure, among other indications.

Neutral endopeptidase (EC 3.4.24.11; enkephalinase; atriopeptidase; NEP) is a zinc-containing metalloprotease that cleaves a variety of peptide substrates on the amino side of hydrophobic residues [see *Pharmacol Rev*, Vol. 45, p. 87 (1993)]. Substrates for this enzyme include, but are not limited to, atrial natriuretic peptide (ANP, also known as ANF), brain natriuretic peptide (BNP), met- and leu-enkephalin, bradykinin, neurokinin A, endothelin-1 and substance P. ANP is a potent vasorelaxant and natriuretic agent [see *J Hypertens*, Vol. 19, p. 1923 (2001)]. Infusion of ANP in normal subjects resulted in a reproducible, marked enhancement of natriuresis and diuresis, including increases in fractional excretion of sodium, urinary flow rate and glomerular filtration rate [see *J Clin Pharmacol*, Vol. 27, p. 927 (1987)]. However, ANP has a short half-life in circulation, and NEP in kidney cortex membranes has been shown to be the major enzyme responsible for degrading this peptide [see *Peptides*, Vol. 9, p. 173 (1988)]. Thus, inhibitors of NEP (neutral endopeptidase inhibitors, NEPi) should increase plasma levels of ANP and, hence, are expected to induce natriuretic and diuretic effects.

While substances, such as angiotensin receptor blockers and neutral endopeptidase inhibitors may be useful in the control of hypertension, essential hypertension is a polygenic disease and is not always controlled adequately by monotherapy. Approximately 333 million adults in economically developed countries and about 65 million Americans (1 in 3 adults) had high blood pressure in 2000 [see *Lancet*, Vol. 365, p. 217 (2005); and *Hypertension*, Vol. 44, p. 398 (2004)]. Prolonged and uncontrolled hypertensive vascular disease ultimately leads to a variety of pathological changes in target organs, such as the heart and kidney. Sustained hypertension can lead as well to an increased occurrence of stroke. Therefore, there is a strong need to evaluate the efficacy of anti-hypertensive therapy, an examination of additional cardiovascular endpoints, beyond those of blood pressure lowering, to get further insight into the benefits of combined treatment.

The nature of hypertensive vascular diseases is multifactorial. Under certain circumstances, drugs with different mechanisms of action have been combined. However, just considering any combination of drugs having different modes of action does not necessarily lead to combinations with advantageous effects. Accordingly, there is a need for efficacious combination therapy which does not have deleterious side effects.

SUMMARY OF THE INVENTION

In a first aspect, the present invention is directed to a dual-acting compound, such as a supramolecular complex, comprising:
  (a) an angiotensin receptor antagonist;
  (b) a neutral endopeptidase inhibitor (NEPi); and optionally
  (c) a pharmaceutically acceptable cation.

The present invention is also directed to a dual-acting compound, such as a supramolecular complex, obtainable by:
  (i) dissolving an angiotensin receptor antagonist and a neutral endopeptidase inhibitor (NEPi) in a suitable solvent;
  (ii) dissolving a basic compound of Cat in a suitable solvent, wherein Cat is a cation;
  (iii) combining the solutions obtained in steps (i) and (ii);
  (iv) precipitation of the solid, and drying same to obtain the dual-acting compound; or alternatively obtaining the dual-acting compound by exchanging the solvent(s) employed in steps (i) and (ii) by
(iva) evaporating the resulting solution to dryness;
(va) re-dissolving the solid in a suitable solvent;
(via) precipitation of the solid and drying same to obtain the dual-acting compound.

The present invention is also directed to linked pro-drugs comprising:
(a) an angiotensin receptor antagonist or a pharmaceutically acceptable salt thereof; and
(b) a NEPi or a pharmaceutically acceptable salt thereof, wherein the angiotensin receptor antagonist or a pharmaceutically acceptable salt thereof and the NEPi or a pharmaceutically acceptable salt thereof are linked by a linking moiety.

The present invention is also directed to a combination comprising:
(a) a pharmaceutically acceptable salt of an angiotensin receptor antagonist; and
(b) a pharmaceutically acceptable salt of a neutral endopeptidase inhibitor (NEPi);
wherein the pharmaceutically acceptable salt of the angiotensin receptor antagonist and the NEPi is the same and is selected from a salt of Na, K or $NH_4$.

In preferred embodiments, the angiotensin receptor antagonist and NEPi have acidic groups which facilitate formation of the dual acting compound, such as the supramolecular complex of the present invention.

Preferably, the angiotensin receptor antagonist is selected from the group consisting of valsartan, losartan, irbesartan, telmisartan, eprosartan, candesartan, olmesartan, saprisartan, tasosartan, elisartan and combinations thereof.

In preferred embodiments, the NEPi is selected from the group consisting of: SQ 28,603; N—[N-[1(S)-carboxyl-3-phenylpropyl]-(S)-phenylalanyl]-(S)-isoserine; N—[N-[((1S)-carboxy-2-phenyl)ethyl]-(S)-phenylalanyl]-β-alanine; N-[2(S)-mercaptomethyl-3-(2-methylphenyl)-propionyl]methionine; (cis-4-[[[1-[2-carboxy-3-(2-methoxyethoxy)propyl]-cyclopentyl]carbonyl]amino]-cyclohexanecarboxylic acid); thiorphan; retro-thiorphan; phosphoramidon; SQ 29072; N-(3-carboxy-1-oxopropyl)-(4S)-p-phenylphenylmethyl)-4-amino-2R-methylbutanoic acid ethyl ester; (S)-cis-4-[1-[2-(5-indanyloxycarbonyl)-3-(2-methoxyethoxy)propyl]-1-cyclopentanecarboxamido]-1-cyclohexanecarboxylic acid; 3-(1-[6-endo-hydroxymethyl-bicyclo[2,2,1]heptane-2-exo-carbamoyl]cyclopentyl)-2-(2-methoxyethyl)propanoic acid; N-(1-(3-(N-t-butoxycarbonyl-(S)-prolylamino)-2(S)-t-butoxy-carbonylpropyl)cyclopentanecarbonyl)-O-benzyl-(S)-serine methyl ester; 4-[[2-(mercaptomethyl)-1-oxo-3-phenylpropyl]amino]benzoic acid; 3-[1-(cis-4-carboxycarbonyl-cis-3-butylcyclohexyl-r-1-carbamoyl)cyclopentyl]-2S-(2-methoxyethoxymethyl)propanoic acid; N-((2S)-2-(4-biphenylmethyl)-4-carboxy-5-phenoxyvaleryl)glycine; N-(1-(N-hydroxycarbamoylmethyl)-1-cyclopentanecarbonyl)-L-phenylalanine; (S)-(2-biphenyl-4-yl)-1-(1H-tetrazol-5-yl)ethylamino) methylphosphonic acid; (S)-5-(N-(2-(phosphonomethylamino)-3-(4-biphenyl)propionyl)-2-aminoethyl)tetrazole; β-alanine; 3-[1,1'-biphenyl]-4-yl-N-[diphenoxyphosphinyl)methyl]-L-alanyl; N-(2-carboxy-4-thienyl)-3-mercapto-2-benzylpropanamide; 2-(2-mercaptomethyl-3-phenylpropionamido)thiazol-4-ylcarboxylic acid; (L)-(1-((2,2-dimethyl-1,3-dioxolan-4-yl)-methoxy)carbonyl)-2-phenylethyl)-L-phenylalanyl)-β-alanine; N—[N-[(L)-[1-[(2,2-dimethyl-1,3-dioxolan-4-yl)-methoxy]carbonyl]-2-phenylethyl]-L-phenylalanyl]-(R)-alanine; N—[N-[(L)-1-carboxy-2-phenylethyl]-L-phenylalanyl]-(R)-alanine; N-[2-acetylthiomethyl-3-(2-methyl-phenyl)propionyl]-methionine ethyl ester; N-[2-mercaptomethyl-3-(2-methylphenyl)propionyl]-methionine; N-[2(S)-mercaptomethyl-3-(2-methylphenyl)propanoyl]-(S)-isoserine; N—(S)-[3-mercapto-2-(2-methylphenyl)propionyl]-(S)-2-methoxy-(R)-alanine; N-[1-[[1(S)-benzyloxycarbonyl-3-phenylpropyl]amino]cyclopentylcarbonyl]-(S)-isoserine; N-[1-[[1(S)-carbonyl-3-phenylpropyl]amino]-cyclopentylcarbonyl]-(S)-isoserine; 1,1'-[dithiobis-[2(S)-(2-methylbenzyl)-1-oxo-3,1-propanediyl]]bis-(S)-isoserine; 1,1'-[dithiobis-[2(S)-(2-methylbenzyl)-1-oxo-3,1-propanediyl]]-bis-(S)-methionine; N-(3-phenyl-2-(mercaptomethyl)-propionyl)-(S)-4-(methylmercapto)methionine; N-[2-acetylthiomethyl-3-phenyl-propionyl]-3-aminobenzoic acid; N-[2-mercaptomethyl-3-phenyl-propionyl]-3-aminobenzoic acid; N-[1-(2-carboxy-4-phenylbutyl)-cyclopentane-carbonyl]-(S)-isoserine; N-[1-(acetylthiomethyl)cyclopentane-carbonyl]-(S)-methionine ethyl ester; 3(S)-[2-(acetylthiomethyl)-3-phenyl-propionyl]amimo-ε-caprolactam; N-(2-acetylthiomethyl-3-(2-methylphenyl) propionyl)-methionine ethyl ester; and combinations thereof. Preferably, the dual-acting compound or combination, in particular the supramolecular complex, is a mixed salt or a co-crystal. It is also preferred that the linked pro-drug is a mixed salt or a co-crystal.

In a second aspect, the present invention is directed to pharmaceutical composition comprising
(a) the aforementioned dual-acting compound or combination, such as the aforementioned complex; and
(b) at least one pharmaceutically acceptable additive.

The present invention is also directed to pharmaceutical compositions comprising a linked pro-drug comprising:
(a) an angiotensin receptor antagonist or a pharmaceutically acceptable salt thereof;
(b) a NEPi or a pharmaceutically acceptable salt thereof, wherein the angiotensin receptor antagonist or a pharmaceutically acceptable salt thereof and the NEPi or a pharmaceutically acceptable salt thereof are linked by a linking moiety; and
(c) at least one pharmaceutically acceptable additive.

In a third aspect, the present invention is directed to a method of preparing a dual-acting compound, in particular a supramolecular complex, comprising
(a) an angiotensin receptor antagonist;
(b) a neutral endopeptidase inhibitor (NEPi); and optionally
(c) a pharmaceutically acceptable cation selected from the group consisting of Na, K and $NH_4$;
said method comprising the steps of:
(i) dissolving an angiotensin receptor antagonist and a neutral endopeptidase inhibitor (NEPi) in a suitable solvent;
(ii) dissolving a basic compound of Cat in a suitable solvent, wherein Cat is a cation;
(iii) combining the solutions obtained in steps (i) and (ii);
(iv) precipitation of the solid, and drying same to obtain the dual-acting compound; or alternatively
obtaining the dual-acting compound by exchanging the solvent(s) employed in steps (i) and (ii) by
(iva) evaporating the resulting solution to dryness;
(va) re-dissolving the solid in a suitable solvent;
(via) precipitation of the solid and drying same to obtain the dual-acting compound.

The present invention is also directed to a method of making a linked pro-drug comprising:
(a) an angiotensin receptor antagonist or a pharmaceutically acceptable salt thereof;

(b) a NEPi or a pharmaceutically acceptable salt thereof, wherein the angiotensin receptor antagonist or a pharmaceutically acceptable salt thereof and the NEPi or a pharmaceutically acceptable salt thereof are linked by a linking moiety; and comprising adding a linking moiety and a solvent to a mixture of an angiotensin receptor antagonist and a NEPi; and (d) isolating the linked pro-drug.

In a fourth aspect, this invention is directed to a method of treating or preventing a disease or condition, such as hypertension, heart failure (acute and chronic), congestive heart failure, left ventricular dysfunction and hypertrophic cardiomyopathy, diabetic cardiac myopathy, supraventricular and ventricular arrhythmias, atrial fibrillation, atrial flutter, detrimental vascular remodeling, myocardial infarction and its sequelae, atherosclerosis, angina (unstable or stable), renal insufficiency (diabetic and non-diabetic), heart failure, angina pectoris, diabetes, secondary aldosteronism, primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, other vascular disorders, such as migraine, peripheral vascular disease, Raynaud's disease, luminal hyperplasia, cognitive dysfunction (such as Alzheimer's), glaucoma and stroke comprising administering the afore-mentioned dual-acting compound or combination, in particular the supramolecular complex, or the aforementioned linked pro-drug, preferably, the complex, to a subject in need of such treatment.

BRIEF DESCRIPTION OF THE DRAWING

FIG. 1 shows a pictorial representation of the unit cell of the supramolecular complex of trisodium [3-((1S,3R)-1-biphenyl-4-ylmethyl-3-ethoxycarbonyl-1-butylcarbamoyl) propionate-(S)-3'-methyl-2'-(pentanoyl{2''-(tetrazol-5-ylate)biphenyl-4'-ylmethyl}amino)butyrate]hemipentahydrate comprising two asymmetric units. The following color code is used: grey=carbon atom; blue=nitrogen atom; red=oxygen atom; violet=sodium atom.

DETAILED DESCRIPTION

The present invention relates to a dual-acting compound or combination, in particular a supramolecular complex, or linked pro-drug or in particular a supramolecular complex of two active agents with different mechanisms of action, namely an angiotensin receptor antagonist and a neutral endopeptidase inhibitor, which can form a unique molecular entity for the treatment of patients with various cardiovascular and/or renal diseases.

One embodiment of the invention is directed to a physical combination comprising:
  (a) a pharmaceutically acceptable salt of an angiotensin receptor antagonist; and
  (b) a pharmaceutically acceptable salt of a neutral endopeptidase inhibitor (NEPi);
wherein the pharmaceutically acceptable salt of the angiotensin receptor antagonist and the NEPi is the same and is selected from a salt of Na, K or NH$_4$.

Specifically, it is preferred that the two active agents are combined with each other so as to form a single dual-acting compound, in particular a supramolecular complex. By doing so, a new molecular or supramolecular entity is formed having distinct properties different to the above physical combination.

Thus, the present invention is directed to a dual-acting compound, in particular a supramolecular complex, comprising:
  (a) an angiotensin receptor antagonist;
  (b) a neutral endopeptidase inhibitor (NEPi); and
  (c) a pharmaceutically acceptable cation preferably selected from the group consisting of Na, K and NH$_4$.

The present invention is also directed to a dual-acting compound, in particular a supramolecular complex, obtainable by:
  (i) dissolving an angiotensin receptor antagonist and a neutral endopeptidase inhibitor (NEPi) in a suitable solvent;
  (ii) dissolving a basic compound of Cat such as (Cat)OH, (Cat)$_2$CO$_3$, (Cat)HCO$_3$ in a suitable solvent, wherein Cat is a cation preferably selected from the group consisting of Na, K and NH$_4$;
  (iii) combining the solutions obtained in steps (i) and (ii);
  (iv) precipitation of the solid, and drying same to obtain the dual-acting compound; or alternatively
obtaining the dual-acting compound by exchanging the solvent(s) employed in steps (i) and (ii) by
  (iva) evaporating the resulting solution to dryness;
  (va) re-dissolving the solid in a suitable solvent;
  (via) precipitation of the solid and drying same to obtain the dual-acting compound.

The present invention is further directed to linked pro-drugs comprising:
  (a) an angiotensin receptor antagonist or a pharmaceutically acceptable salt thereof; and
  (b) a NEPi or a pharmaceutically acceptable salt thereof, wherein the angiotensin receptor antagonist or a pharmaceutically acceptable salt thereof and the NEPi or a pharmaceutically acceptable salt thereof are linked by a linking moiety.

The two components are each linked to a linking moiety thereby creating a linked pro-drug. Preferably, the linked pro-drug is substantially pure; as used herein, "substantially pure" refers to at least 90%, more preferably at least 95% and most preferably at least 98% purity.

As one preferred embodiment of the present invention, the linked pro-drug has a structure such that by linking the two components with the linking moiety, a supramolecular complex is formed. For the purpose of the present invention, the term "dual-acting compound" is intended to describe that these compounds have two different modes of action in one compound, one is the angiotensin receptor blockade resulting from the ARB molecular moiety of the compound and the other is the neutral endopeptidase inhibition resulting from the NEPi molecular moiety of the compound.

For the purpose of the present invention, the term "compound" is intended to describe a chemical substance comprising covalent bonds within the two pharmaceutically active agents, the ARB and the NEPi molecular moieties, and non-covalent interactions between these two pharmaceutically active agents, the ARB and the NEPi molecular moieties. Typically, hydrogen bonding can be observed between the two pharmaceutically active agents, the ARB and the NEPi molecular moieties. Ionic bonds can be present between the cation and one or both of the two pharmaceutically active agents, the ARB and the NEPi molecular moieties. Other types of bonds may also be present within the compound such as van der Waals forces. For illustrative purposes, the dual-acting compound of the present invention could be represented as follows:

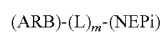

(ARB)-(L)$_m$-(NEPi)

wherein L is a linking moiety, such as a cation or is a noncovalent bond and m is an integer from 1 or more. In other words the ARB and NEPi moiety can be connected via non-covalent bonds such as hydrogen bonding. Alternatively or additionally they may be connected via a linking moiety such as a cation.

In one embodiment, the dual-acting compound may be considered to be a linked pro-drug, whereby the linking moiety, such as the cation, linking the two pharmaceutically active agents, the ARB and the NEPi, forms the pro-drug of these agents which are released once the linked pro-drug is ingested and absorbed.

In a preferred embodiment, the dual-acting compound is a complex, in particular a supramolecular complex.

For the purpose of the present invention, the term "supramolecular complex" is intended to describe an interaction between the two pharmaceutically active agents, the cations and any other entity present such as a solvent, in particular water, by means of noncovalent, intermolecular bonding between them. This interaction leads to an association of the species present in the supramolecular complex distinguishing this complex over a physical mixture of the species.

The noncovalent intermolecular bonding can be any interactions known in the art to form such supramolecular complexes, such as hydrogen bonding, van der Waals forces and π-π stacking. Ionic bonds can also be present. Preferably, there exists ionic bonding and additionally hydrogen bonding to form a network of interactions within the complex. The supramolecular complex exists preferably in the solid state but may also be present in liquid media. As a preferred embodiment of the invention, the complex is crystalline and in this case is preferably a mixed crystal or co-crystal.

Typically, the dual-acting compound, in particular the supramolecular complex shows properties such as melting point, IR spectrum etc. that are different from a physical mixture of the species.

Preferably, the dual-acting compound, in particular the supramolecular complex, has a network of non-covalent bonds, in particular hydrogen bonds, between the two pharmaceutically active agents and any solvent, if present, preferably water. Moreover, it is preferred that the dual-acting compound, in particular the supramolecular complex, has a network of non-covalent bonds, in particular ionic and hydrogen bonds, between the two pharmaceutically active agents, the cation and any solvent, if present, preferably water. The cation is preferably coordinated to several oxygen ligands, thus, providing a linkage between these oxygen ligands. The oxygen ligands come from the carbonyl and carboxylate groups present in the two pharmaceutically active agents and preferably also from any solvent, if present, preferably water.

The dual acting compound comprises a molecular moiety of an angiotensin receptor antagonist. This means that a molecular moiety derived from an angiotensin receptor antagonist is participating in the build-up of the dual-acting compound. The angiotensin receptor antagonist is part of the compound and connected to the NEP inhibitor directly or indirectly via non-covalent bonds. For sake of convenience, throughout the application, the term "angiotensin receptor antagonist" will be used when describing this part of the compound. Angiotensin receptor antagonists (ARBs) suitable for use in the present invention include, without limitation, valsartan, losartan, irbesartan, telmisartan, eprosartan, candesartan, olmesartan saprisartan, tasosartan, elisartan, the compound with the designation E-1477 of the following formula

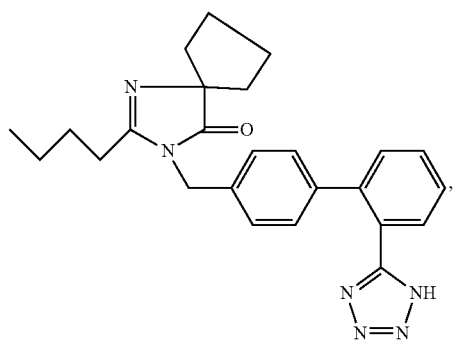 [SMILES: CCCCC1=NC2(CCCC2)C(=O)N1Cc1ccc(-c2ccccc2-c2nnn[nH]2)cc1]

the compound with the designation SC-52458 of the following formula

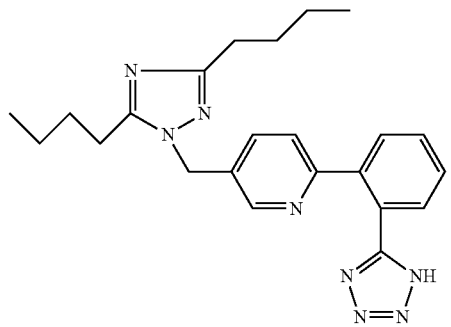 [SMILES: CCCCc1nc(CCCC)n(Cc2ccc(-c3ccccc3-c3nnn[nH]3)nc2)n1]

and the compound with the designation the compound ZD-8731 of the following formula

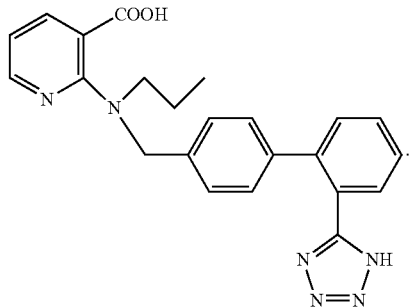 [SMILES: CCCN(Cc1ccc(-c2ccccc2-c2nnn[nH]2)cc1)c1ncccc1C(=O)O]

Suitable angiotensin II receptor antagonist also includes, but is not limited to, saralasin acetate, candesartan cilexetil, CGP-63170, EMD-66397, KT3-671, LR-B/081, valsartan, A-81282, BIBR-363, BIBS-222, BMS-184698, candesartan, CV-11194, EXP-3174, KW-3433, L-161177, L-162154, LR-B/057, LY-235656, PD-150304, U-96849, U-97018, UP-275-22, WAY-126227, WK-1492.2K, YM-31472, losartan potassium, E-4177, EMD-73495, eprosartan, HN-65021, irbesartan, L-159282, ME-3221, SL-91.0102, Tasosartan, Telmisartan, UP-269-6, YM-358, CGP-49870, GA-0056, L-159689, L-162234, L-162441, L-163007, PD-123177, A-81988, BMS-180560, CGP-38560A, CGP-48369, DA-2079, DE-3489, DuP-167, EXP-063, EXP-6155, EXP-6803, EXP-7711, EXP-9270, FK-739, HR-720, ICI-D6888, ICI-D7155, ICI-D8731, isoteoline, KRI-1177, L-158809, L-158978, L-159874, LR B087, LY-285434, LY-302289, LY-315995, RG-13647, RWJ-38970, RWJ-46458, S-8307, S-8308, saprisartan, saralasin, Sarmesin, WK-1360, X-6803, ZD-6888, ZD-7155, ZD-8731, BIBS39, C1-996, DMP-811, DuP-532, EXP-929, L-163017, LY-301875, XH-148, XR-510, zolasartan and PD-123319.

Also included within the scope of this aspect of the invention are combinations of the above-identified ARBs.

ARBs to be used for preparing the combination or complex in accordance with the present invention can be purchased from commercial sources or can be prepared according to known methods. ARBs may be used for purposes of this invention in their free form, as well as in any suitable salt or ester form.

Preferred salts forms include acid addition salts. The compounds having at least one acid group (e.g., COOH or 5-tetrazolyl) can also form salts with bases. Suitable salts with bases are, e.g., metal salts, such as alkali metal or alkaline earth metal salts, e.g., sodium, potassium, calcium or magnesium salts, or salts with ammonia or an organic amine, such as morpholine, thiomorpholine, piperidine, pyrrolidine, a mono-, di- or tri-lower alkylamine, e.g., ethyl-, tert-butyl-, diethyl-, diisopropyl-, triethyl-, tributyl- or dimethylpropylamine, or a mono-, di- or trihydroxy lower alkylamine, e.g., mono-, di- or tri-ethanolamine. Corresponding internal salts may furthermore be formed. Salts which are unsuitable for pharmaceutical uses but which can be employed, e.g., for the isolation or purification of free compounds I or their pharmaceutically acceptable salts, are also included. Even more preferred salts are, e.g., selected from the mono-sodium salt in amorphous form; di-sodium salt of valsartan in amorphous or crystalline form, especially in hydrate form, thereof.

Mono-potassium salt of valsartan in amorphous form; di-potassium salt of valsartan in amorphous or crystalline form, especially in hydrate form, thereof.

Calcium salt of valsartan in crystalline form, especially in hydrate form, primarily the tetrahydrate thereof; magnesium salt of valsartan in crystalline form, especially in hydrate form, primarily the hexahydrate thereof; calcium/magnesium mixed salt of valsartan in crystalline form, especially in hydrate form; bis-diethylammonium salt of valsartan in crystalline form, especially in hydrate form; bis-dipropylammonium salt of valsartan in crystalline form, especially in hydrate form; bis-dibutylammonium salt of valsartan in crystalline form, especially in hydrate form, primarily the hemihydrate thereof; mono-L-arginine salt of valsartan in amorphous form; bis-L-arginine salt of valsartan in amorphous form; mono-L-lysine salt of valsartan in amorphous form; bis-L-lysine salt of valsartan in amorphous form.

Preferably when preparing the dual-acting compound, in particular the complex according to the present invention, the free form of the ARB is used.

In a preferred embodiment of this invention, the angiotensin receptor blocker used in the combination or complex of the present invention is Valsartan the molecular structure of which is shown below

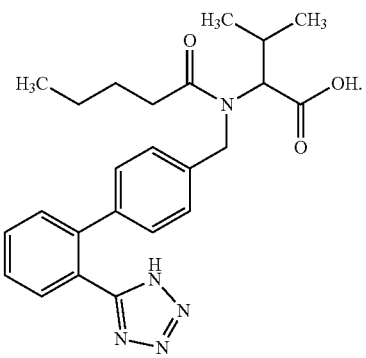 [SMILES: CCCCC(=O)N(Cc1ccc(-c2ccccc2-c2nnn[nH]2)cc1)C(C(=O)O)C(C)C]

Valsartan may be in the racemic form or as one of the two isomers shown below

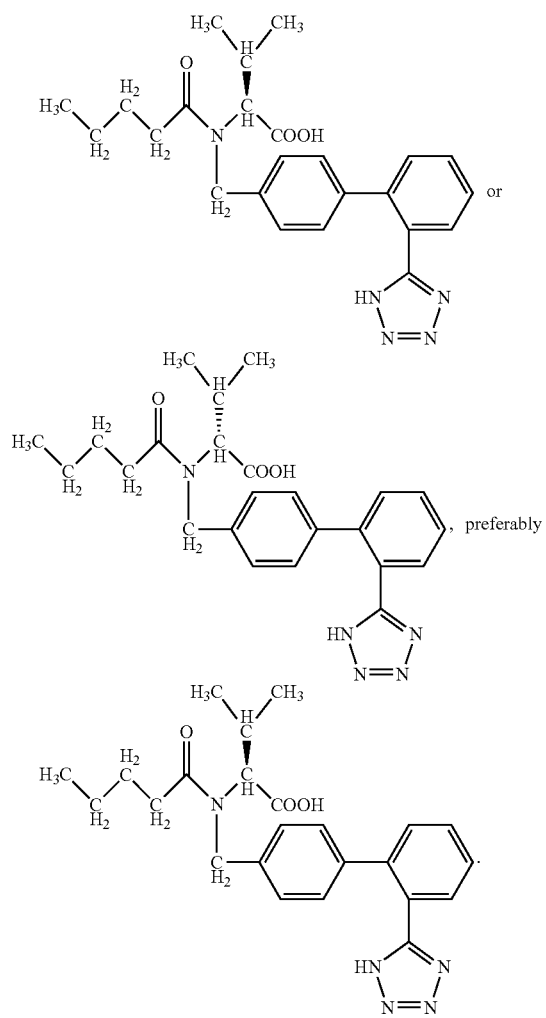

Valsartan ((S)—N-valeryl-N-{[2'-(1H-tetrazole-5-yl)-biphenyl-4-yl]-methyl}-valine) used according to the present invention can be purchased from commercial sources or can be prepared according to known methods. For example, the preparation of valsartan is described in U.S. Pat. No. 5,399,578 and EP 0 443 983, the entire disclosure of each of which is incorporated by reference herein. Valsartan may be used for purposes of this invention in its free acid form, as well as in any suitable salt form. Additionally, esters or other derivatives of the carboxylic grouping may be applied for the synthesis of linked pro-drugs, as well as salts and derivatives of the tetrazole grouping. Reference to ARBs includes reference to pharmaceutically acceptable salts thereof.

Preferably, the ARB is a diprotic acid. Thus, the angiotensin receptor blocker has a charge of 0, 1 or 2 depending on the pH of the solution.

In the combination of the present invention, the ARB is in the form of a pharmaceutically acceptable salt selected from Na, K or $NH_4$, preferably Na. This includes both the mono- and di-salt of these cations, preferably the di-salt. In particular in the case of valsartan this means that both the carboxylic acid moiety and the tetrazole moiety form the salt.

In the dual-acting compound, in particular the supramolecular complex of the present invention, typically the free form of the ARB is employed in the preparation and the cationic species present in the complex is introduced by using a base, e.g. (Cat)OH.

The dual acting compound comprises a molecular moiety of a neutral endopeptidase inhibitor. This means that a molecular moiety derived from a neutral endopeptidase inhibitor is participating in the build-up of the dual-acting compound. The neutral endopeptidase inhibitor is part of the compound and connected to the ARB directly or indirectly via non-covalent bonds. For sake of convenience, throughout the application, the term "neutral endopeptidase inhibitor" will be used when describing this part of the compound. Neutral endopeptidase inhibitors suitable for use in the present invention include those of formula (I)

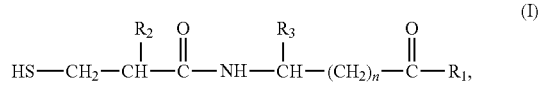

wherein
  $R_2$ is alkyl of 1-7 carbons, trifluoromethyl, phenyl, substituted phenyl, —$(CH_2)$1 to 4-phenyl, or —$(CH_2)$1 to 4-substituted phenyl;
  $R_3$ is hydrogen, alkyl of 1-7 carbons, phenyl, substituted phenyl, —$(CH_2)$1 to 4-phenyl or —$(CH_2)$1 to 4-substituted phenyl;
  $R_1$ is hydroxy, alkoxy of 1-7 carbons or $NH_2$;
  n is an integer from 1-15;
and the term substituted phenyl refers to a substituent selected from lower alkyl of 1-4 carbons, lower alkoxy of 1-4 carbons, lower alkylthio of 1-4 carbons, hydroxy, Cl, Br or F.

Preferred neutral endopeptidase inhibitors of formula (I) include compounds, wherein
  $R_2$ is benzyl;
  $R_3$ is hydrogen;
  n is an integer from 1-9; and
  $R_1$ is hydroxy.

Another preferred neutral endopeptidase inhibitor is (3S,2'R)-3-{1-[2'-(ethoxycarbonyl)-4'-phenyl-butyl]-cyclopentan-1-carbonylamino}-2,3,4,5-tetrahydro-2-oxo-1H-1-benzazepine-1-acetic acid or a pharmaceutically acceptable salt thereof.

Preferred neutral endopeptidase inhibitors suitable for use in the present invention include, without limitation, SQ 28,603; N—[N-[1(S)-carboxyl-3-phenylpropyl]-(S)-phenylalanyl]-(S)-isoserine; N—[N-[((1S)-carboxy-2-phenyl)ethyl]-(S)-phenylalanyl]-β-alanine; N-[2(S)-mercaptomethyl-3-(2-methylphenyl)-propionyl]methionine; (cis-4-[[[1-[2-carboxy-3-(2-methoxyethoxy)propyl]-cyclopentyl]carbonyl]amino]-cyclohexanecarboxylic acid); thiorphan; retro-thiorphan; phosphoramidon; SQ 29072; (2R,4S)-5-biphenyl-4-yl-4-(3-carboxy-propionylamino)-2-methyl-pentanoic acid ethyl ester; N-(3-carboxy-1-oxopropyl)-(4S)-p-phenylphenylmethyl)-4-amino-2R-methylbutanoic acid; (S)-cis-4-[1-[2-(5-indanyloxycarbonyl)-3-(2-methoxy-ethoxy)propyl]-1-cyclopentanecarboxamido]-1-cyclo-hexanecarboxylic acid; 3-(1-[6-endo-hydroxymethylbicyclo [2,2,1]heptane-2-exo-carbamoyl]cyclopentyl)-2-(2-methoxyethyl)propanoic acid; N-(1-(3-(N-t-butoxycarbonyl-(S)-prolylamino)-2(S)-t-butoxy-carbonylpropyl)cyclopentanecarbonyl)-O-benzyl-(S)-serine methyl ester; 4-[[2-(mercaptomethyl)-1-oxo-3-phenylpro-pyl]amino]benzoic acid; 3-[1-(cis-4-carboxycarbonyl-cis-3-butylcyclohexyl-r-1-carbamoyl)cyclopentyl]-2S-(2-methoxyethoxymethyl)propanoic acid; N-((2S)-2-(4-biphenylmethyl)-4-carboxy-5-phenoxyvaleryl)glycine; N-(1-(N-hydroxycarbamoylmethyl)-1-cyclopentanecarbo-nyl)-L-phenylalanine; (S)-(2-biphenyl-4-yl)-1-(1H-tetrazol-5-yl)ethylamino) methylphosphonic acid; (S)-5-(N-(2-(phosphonomethylamino)-3-(4-biphenyl)propionyl)-2-aminoethyl)tetrazole; β-alanine; 3-[1,1'-biphenyl]-4-yl-N-[diphenoxyphosphinyl)methyl]-L-alanyl; N-(2-carboxy-4-thienyl)-3-mercapto-2-benzylpropanamide; 2-(2-mercaptomethyl-3-phenylpropionamido)thiazol-4-ylcarboxylic acid; (L)-(1-((2,2-dimethyl-1,3-dioxolan-4-yl)-methoxy)carbonyl)-2-phenylethyl)-L-phenylalanyl)-β-alanine; N—[N-[(L)-[1-[(2,2-dimethyl-1,3-dioxolan-4-yl)-methoxy]carbonyl]-2-phenylethyl]-L-phenylalanyl]-(R)-alanine; N—[N-[(L)-1-carboxy-2-phenylethyl]-L-phenylalanyl]-(R)-alanine; N-[2-acetylthiomethyl-3-(2-methyl-phenyl)propionyl]-methionine ethyl ester; N-[2-mercaptomethyl-3-(2-methylphenyl)propionyl]-methionine; N-[2(S)-mercaptomethyl-3-(2-methylphenyl)propanoyl]-(S)-isoserine; N—(S)-[3-mercapto-2-(2-methylphenyl)pro-pionyl]-(S)-2-methoxy-(R)-alanine; N-[1-[[1(S)-benzyloxy-carbonyl-3-phenylpropyl]amino]cyclopentylcarbonyl]-(S)-isoserine; N-[1-[[1(S)-carbonyl-3-phenylpropyl]amino]-cyclopentylcarbonyl]-(S)-isoserine; 1,1'-[dithiobis-[2(S)-(2-methylbenzyl)-1-oxo-3,1-propanediyl]]-bis-(S)-isoserine; 1,1'-[dithiobis-[2(S)-(2-methylbenzyl)-1-oxo-3,1-pro-panediyl]]-bis-(S)-methionine; N-(3-phenyl-2-(mercaptom-ethyl)-propionyl)-(S)-4-(methylmercapto)methionine; N-[2-acetylthiomethyl-3-phenyl-propionyl]-3-aminobenzoic acid; N-[2-mercaptomethyl-3-phenyl-propionyl]-3-amino-benzoic acid; N-[1-(2-carboxy-4-phenylbutyl)-cyclopen-tane-carbonyl]-(S)-isoserine; N-[1-(acetylthiomethyl)cyclo-pentane-carbonyl]-(S)-methionine ethyl ester; 3(S)-[2-(acetylthiomethyl)-3-phenyl-propionyl]amimo-ε-caprolactam; N-(2-acetylthiomethyl-3-(2-methyl phenyl) propionyl)-methionine ethyl ester; and combinations thereof.

Neutral endopeptidase inhibitors can be purchased from commercial sources or can be prepared according to known methods, such as those set forth in any of U.S. Pat. Nos. 4,722,810, 5,223,516, 4,610,816, 4,929,641, South African Patent Application 84/0670, UK 69578, U.S. Pat. No. 5,217,996, EP 00342850, GB 02218983, WO 92/14706, EP 00343911, JP 06234754, EP 00361365, WO 90/09374, JP 07157459, WO 94/15908, U.S. Pat. Nos. 5,273,990, 5,294,632, 5,250,522, EP 00636621, WO 93/09101, EP 00590442, WO 93/10773, U.S. Pat. No. 5,217,996, the disclosure of each of which is incorporated by reference. Neutral endopeptidase inhibitors may be used for purposes of this invention in their free form, as well as in any suitable salt form. Reference to neutral endopeptidase inhibitors includes reference to pharmaceutically acceptable salts thereof.

Additionally esters or other derivatives of any carboxylic grouping may be applied for the synthesis of linked pro-drugs, as well as salts and derivatives of any other acidic grouping. In a preferred embodiment of this invention, the NEPi is 5-biphenyl-4-yl-4-(3-carboxy-priopionylamino)-2-methyl-pentanoic acid ethyl ester of formula (II) or the respective hydrolysed form 5-biphenyl-4-yl-4-(3-carboxy-priopionylamino)-2-methyl-pentanoic acid.

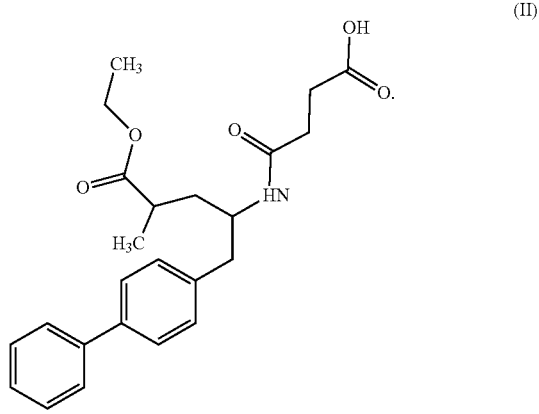 [SMILES: CCOC(=O)C(C)CC(Cc1ccc(-c2ccccc2)cc1)NC(=O)CCC(=O)O]

The compound of formula (II) can exist as the (2R,4S), (2R,4S), (2R,4S) or (2R,4S) isomer. Preferred is (2R,4S)-5-biphenyl-4-yl-4-(3-carboxy-propionylamino)-2-methyl-pentanoic acid ethyl ester as shown below:

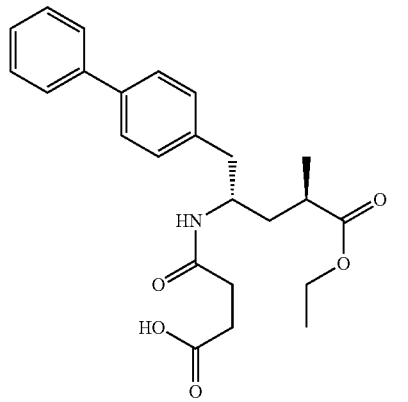 [SMILES: CCOC(=O)[C@H](C)C[C@@H](Cc1ccc(-c2ccccc2)cc1)NC(=O)CCC(=O)O]

The compound of formula (II) is a specific inhibitor of NEP and is described in U.S. Pat. No. 5,217,996. It can be purchased from commercial sources or can be prepared according to known methods. The compound of formula (II) may be used for purposes of this invention in its free form, as well as in any suitable salt or ester form.

Preferably the NEPi is a monoprotic acid. Thus, the NEPi has a charge of 0 or 1 depending on the pH of the solution.

In the combination of the present invention, the NEPi is in the form of a pharmaceutically acceptable salt selected from Na, K or $NH_4$, preferably Na.

In the dual-acting compound, in particular the supramolecular complex of the present invention, typically the free form of the NEPi is employed in the preparation and the cationic species present in the complex is introduced by using a base, (Cat)OH.

The dual acting compound preferably comprises non-covalent bonds between the ARB and the NEPi. Alternatively or in addition, it optionally comprises a linking moiety such as a pharmaceutically acceptable cation.

The linking moiety includes, but is not limited to, generally regarded as safe (GRAS) compounds or other pharmacologically acceptable compounds. The linking moiety may be an ion or a neutral molecule. In the case wherein the linking moiety is an ion the linked pro-drug is a salt and when the linking moiety is a neutral molecule the linked pro-drug is a co-crystal. Without being bound by any particular theory, the acidic portion of the ARB and NEPi donate a proton to the basic linking moiety such that all three components then become united to form one molecule. When the linked pro-drug is ingested by the subject intended to be treated the more acidic nature of the ingestion environment causes the linked pro-drug to separate into individual components concomitant with ingestion and absorption and therefore be converted into active agents to provide their beneficial biological action to treat the intended diseases.

In the case of a linked pro-drug salt or the dual-acting compound, the linking moiety or the cation, respectively, is preferably a positively charged mono-, di- or tri-valent cation, an organic base or an amino acid. Preferred cations (Cat) both for the linked pro-drug in general and the dual-acting compound, in particular the complex are basic cations, even more preferably metallic cations. Preferred metallic cations include, but are not limited to Na, K, Ca, Mg, Zn, Fe or $NH_4$. Amine bases and salt forming agents may also be employed, such as benzathine, hydrabamine, ethylenediamine, n-n-dibenzyl-ethylenediamine, L-arginine, choline hydroxide, N-methyl-glucamine, (Meglumine), L-Lysine, dimethylaminoethanol (Deanol), t-butylamine, diethylamine, 2-(diethylamino)-ethanol, 4-(2-hydroxyethyl)-morpholine, Thromethanine (TRIS), 4-acetamidophenol, 2-amino-2-methyl-1,3-propanediol, 2-amino-2-methyl-propanol, benzylamine, cyclohexylamine, diethanolamine, ethanolamine, imidazole, piperazine and triethanolamine.

Most preferably, the cation is Na, K or $NH_4$, such as Na. In one embodiment Ca is preferred.

In the case of a linked pro-drug co-crystal, the linking moiety is may also be a neutral molecule which provides hydrogen-bonding functionality.

In one embodiment, the linked pro-drugs of this invention are represented as set forth below, wherein scheme (1) and (2) represent a salt and scheme (3) represents a co-crystal:

NEPi.Xa.ARB           scheme (1)

NEPi.XaYb.ARB        scheme (2)

NEPi.Zc.ARB           scheme (3), wherein
X is Ca, Mg, Zn or Fe;
Y is Na, K or NH4;
Z is a neutral molecule; and
a, b and c reflect the stoichiometry of the linked pro-drug, preferably, a, b and c are a valence of $1^+$, $2^+$ or $3^+$.

For the linked pro-drugs of schemes (1) and (2), above, preferably the NEPi is a monoprotic acid and ARB is a diprotic acid. The angiotensin receptor blocker has a charge of 0, 1 or 2 and the NEPi has a charge of 0 or 1 depending on the pH of the solution, while the overall molecule will be neutral. Ratios of ARB to NEPi will be 1:1, 1:2, 1:3, 3:1, 2:1, 1:1, preferably 1:1, 1:2 or 1:3, most preferably 1:1.

Multi-component salts, particularly with zinc and calcium have been reported in the literature, e.g., Chem Pharm Bull, Vol. 53, p. 654 (2005). These ions require a coordination geometry that facilitates the crystallization of multi-component systems. The metal ions have coordinating geometries governed by the atomic orbitals for each species Valsartan comprises two acidic groupings: the carboxylic acid and the tetrazole. In one embodiment of this aspect of the present invention, the molecular structure of linked pro-drugs of valsartan and a NEPi comprise a linkage between the carboxylic acid and the linking moiety or a linkage between the tetrazole grouping and the linking moiety. In yet another embodiment, the linked pro-drug comprises a trivalent linking moiety linked to the valsartan carboxylic acid grouping, the tetrazole grouping and the NEPi grouping.

In an embodiment of this aspect of the invention, valsartan is linked to (2R,4S)-5-biphenyl-4-yl-4-(3-carboxy-propionylamino)-2-methyl-pentanoic acid ethyl ester by a calcium salt ion.

In a preferred embodiment of the present application, the angiotensin receptor antagonist and the neutral endopeptidase inhibitor are present in a molar ratio of 1:1, 1:2, 1:3, 3:1, 2:1, more preferably 1:1 in the combination as well as in the supramolecular complex. This is also true for the linked pro-drug. Moreover, in the complex, angiotensin receptor antagonist, the neutral endopeptidase inhibitor and the cation are present in a molar ratio of 1:1:1, 1:1:2, 1:1:3, more preferably 1:1:3. This applies equally to the linked pro-drug.

The combination or the dual-acting compound, in particular the complex of the present invention may contain a solvent. This is particularly preferred in the case of the dual-acting compound, in particular the complex, where the solvent may contribute to the intermolecular structure, e.g. the supramolecular interactions. Preferred solvents include water, methanol, ethanol, 2-propanol, acetone, ethyl acetate, methyl-t-butylether, acetonitrile, toluene, and methylene chloride, preferably water. If a solvent is present, one or more molecules per molecule of the active agent can be present. In this case, namely if a stoichiometric amount of the solvent is present, preferably 1, 2, 3, 4 or 5, more preferably 3, molecules of solvent, such as water, can be present per molecule of active agent. Alternatively, the solvent may be present in non-stoichiometric amounts. This means preferably any stoichiometric fraction of the solvent, such as 0.25, 0.5, 0.75, 1.25, 1.5, 1.75, 2.25, 2.5, 2.75, 3.25, 3.5, 3.75, 4.25, 4.5 and 4.75, preferably 2.5, molecules of solvent, such as water, can be present per molecule of active agent. If the dual-acting compound, in particular the complex is in the crystalline form, the solvent may be part of the molecular packing and be trapped in the crystal lattice.

Thus in a preferred embodiment of the present invention, the dual-acting compound, in particular the supramolecular complex is described by the sum formula:

[ARB(NEPi)]Na$_{1-3}$.xH$_2$O, wherein x is 0, 1, 2 or 3, such as 3, preferably

[ARB(NEPi)]Na$_3$.xH$_2$O, wherein x is 0, 1, 2 or 3, such as 3, more preferably

[valsartan ((2R,4S)-5-biphenyl-4-yl-4-(3-carboxy-propionylamino)-2-methyl-pentanoic acid ethyl ester)]Na$_3$.x H$_2$O, wherein x is 0, 1, 2 or 3, such as 3.

Thus in a preferred embodiment of the present invention, the dual-acting compound, in particular the supramolecular complex is described by the sum formula:

[ARB(NEPi)]Na$_{1-3}$.xH$_2$O, wherein x is 0 to 3, such as 2.5, preferably

[ARB(NEPi)]Na$_3$.xH$_2$O, wherein x is 0 to 3, such as 2.5, more preferably

[(N-valeryl-N-{[2'-(1H-tetrazole-5-yl)-biphenyl-4-yl]-methyl}-valine) (5-biphenyl-4-yl-4-(3-carboxy-priopionylamino)-2-methyl-pentanoic acid ethyl ester]Na$_3$.x H$_2$O, in particular [((S)—N-valeryl-N-{[2'-(1H-tetrazole-5-yl)-biphenyl-4-yl]-methyl}-valine) ((2R,4S)-5-biphenyl-4-yl-4-(3-carboxy-propionylamino)-2-methyl-pentanoic acid ethyl ester]Na$_3$.x H$_2$O, wherein x is 0 to 3, such as 2.5. In this most preferred example, the complex is termed trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate.

A simplified structure of trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate used to formally calculate the relative molecular mass, is shown below.

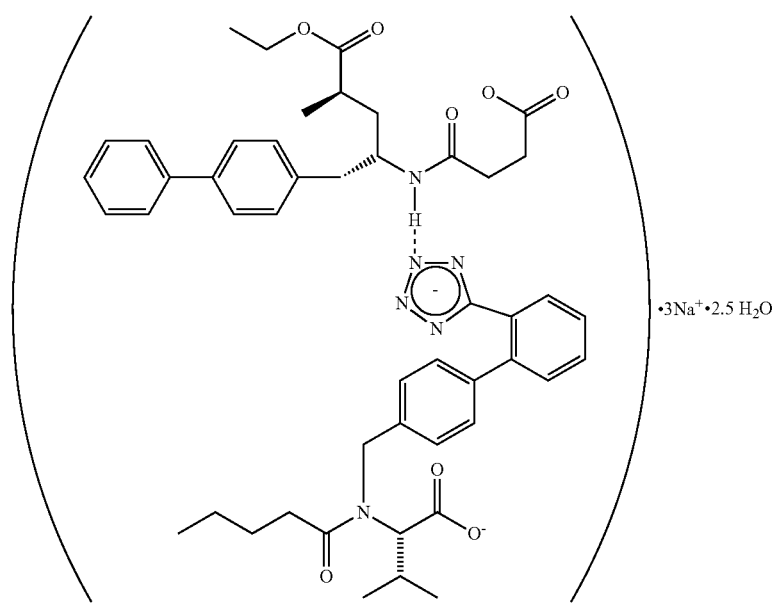

Valsartan comprises two acidic groupings: the carboxylic acid and the tetrazole. In one embodiment of this aspect of the present invention, the molecular structure of the dual-acting compound, in particular, the complex, of valsartan and a NEPi comprises an interaction between the carboxylic acid and the cation, such as Na, or the solvent, such as water, or a linkage between the tetrazole grouping and the cation, such as Na, or the solvent, such as water. In yet another embodiment, the dual-acting compound, in particular, the complex, comprises an interaction between the valsartan carboxylic acid grouping, the tetrazole grouping or the NEPi grouping and the cation, such as Na, or the solvent, such as water.

The combination or dual-acting compound, in particular, the complex, of the present invention is preferably in the solid form. In the solid state it can be in the crystalline, partially crystalline, amorphous, or polymorphous form, preferably in the crystalline form.

The dual-acting compound, in particular, the complex, of the present invention is distinct from a combination of an ARB and a NEPi obtained by simply physically mixing the two active agents. Thus, it can have different properties that make it particularly useful for manufacturing and therapeutic applications. The difference of the dual-acting compound, in particular, the complex, and the combination can be exemplified by the dual-acting compound of (S)—N-valeryl-N-{[2'-(1H-tetrazole-5-yl)-biphenyl-4-yl]-methyl}-valine and (2R,4S)-5-biphenyl-4-yl-4-(3-carboxy-propionylamino)-2-methyl-pentanoic acid ethyl ester which is characterized by very distinct spectral peaks and shifts that are not observed in the physical mixture.

Specifically, such a dual-acting compound is preferably characterized by an X-ray powder diffraction pattern taken with a Scintag XDS2000 powder diffractometer using Cu-Ka radiation (lamda=1.54056 A) with a Peltier-cooled Silicon detector at room temperature (25 degree C.). Scan range was from 1.5 degree to 40 degree in 2 theta with a scan rate of 3 degree/minute. The most important reflections in the X-ray diffraction diagram comprise the following interlattice plane intervals:

The preferred characterization of trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate is obtained from the interlattice plane intervals d of the ascertained X-ray diffraction diagrams, whereby, in the following, average values $2\Theta$ in [°] are indicated (error limit of ±0.2)

4.5, 5.5, 5.6, 9.9, 12.8, 15.7, 17.0, 17.1, 17.2, 18.3, 18.5, 19.8, 21.5, 21.7, 23.2, 23.3, 24.9, 25.3, 27.4, 27.9, 28.0, 30.2. or with an error limit of ±0.1:
4.45, 5.52, 5.57, 9.94, 12.82, 15.66, 17.01, 17.12, 17.2, 18.32, 18.46, 19.76, 21.53, 21.72, 23.17, 23.27, 24.88, 25.3, 27.4, 27.88, 28.04, 30.2.

The most intensive reflections in the X-ray diffraction pattern show the following interlattice plane intervals:
$2\Theta$ in [°]: .4.5, 5.6, 12.8, 17.0, 17.2, 19.8, 21.5, 27.4, in particular 4.45, 5.57, 17.01, 17.2, 19.76, 21, 27.4.

A preferred method of checking the above-indicated average values of the interlattice plane intervals and intensities measured by experimentation from X-ray diffraction, for a given substance, consists in calculating these intervals and their intensities from the comprehensive single crystal structure determination. This structure determination yields cell constants and atom positions, which enable the X-ray diffraction diagram corresponding to the solid to be calculated by means of computer-aided calculation methods. The program used is Powder Pattern within the application software Materials Studio (Accelrys). A comparison of these data, namely the interlattice plane intervals and intensities of the most important lines of trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate, obtained from measurements and from calculating the single crystal data, is illustrated in the table below.

TABLE

| Measured | | calculated | | measured | | calculated | |
| --- | --- | --- | --- | --- | --- | --- | --- |
| $2\Theta$ in [°] | Intensity | $2\Theta$ in [°] | Intensity | $2\Theta$ in [°] | Intensity | $2\Theta$ in [°] | Intensity |
| 4.45 | very strong | 4.15 | very strong | 19.76 | strong | 19.6 | very weak |
| 5.52 | Strong | 5 | strong | 21.53 | weak | 19.8 | very weak |
| 5.57 | strong | 6.5 | strong | 21.72 | very weak | 21.4 | very weak |
| 9.94 | very weak | 9.75 | weak | 23.17 | weak | 23.1 | very weak |
| 12.82 | very strong | 12.6 | weak | 23.27 | weak | 23.15 | very weak |
| 15.66 | very weak | 15.05 | strong | 24.88 | very weak | | very weak |
| 17.01 | weak | 16.9 | very strong | 25.3 | weak | 25.3 | very weak |
| 17.12 | strong | 17.1 | strong | 27.4 | weak | 27.3 | very weak |
| 17.2 | weak | 17.15 | weak | 27.88 | very weak | 27.9 | very weak |
| 18.32 | weak | 18.25 | very weak | 28.04 | weak | | |
| 18.46 | weak | 18.3 | weak | 30.2 | weak | | |

Relative intensity between 100% to 50% is referred to as very strong, 50% to 10% as strong, 10% to 5% as weak, and below 5% as very weak.

The invention relates to trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate, a crystalline solid which is characterized by the data and parameters obtained from single crystal X-ray analysis and X-ray powder patterns. An in-depth discussion of the theory of the methods of single crystal X-ray diffraction and the definition of the evaluated crystal data and the parameters may be found in Stout & Jensen, X-Ray Structure Determination; A Practical Guide, Mac Millian Co., New York, N.Y. (1968) chapter 3.

Crystal Data

| | |
| --- | --- |
| sum formula | $C_{48}H_{55}N_6O_8Na_3 \cdot 2.5H_2O$ |
| molecular mass | 957.99 |
| crystal colour | colourless |

-continued

| | |
|---|---|
| crystal shape | tabular: hexagonal |
| crystal system | monoclinic |
| space group | P2$_1$ |
| Cell parameters | a = 20.344 Å |
| | b = 42.018 Å |
| | c = 20.374 Å |
| | α = 90° |
| | β = 119.29° |
| | γ = 90° |
| volume of unit cell | 15190.03 Å$^3$ |
| Z (the number of asymmetric units in the unit cell) | 2 |
| calculated density | 1.26845 g/cm$^3$ |

Single Crystal X-ray Measurement Data

| | |
|---|---|
| diffractometer | Nonius KappaCCD |
| X-ray generator | Nonius FR571 X-ray generator with a copper rotating anode |
| temperature | 270K and 150K |

Notes:
Two data sets on two suitable single crystals were collected at two different temperatures to assure no phase change during cooling.
None of the hydrogen atoms on the water or the amine nitrogen atoms were observed in the Fourier maps so they were not included in the refinement.

Notes:

Two data sets on two suitable single crystals were collected at two different temperatures to assure no phase change during cooling.

None of the hydrogen atoms on the water or amine nitrogen atoms were observed in the Fourier maps so they were not included in the refinement.

Computer Program Used to Solve the Structure

SHELXD (Sheldrick, Göttingen)

In three dimensions, the unit cell is defined by three edge lengths a, b, and c, and three interaxial angles α, β, and γ. In this way, the volume of the unit cell $V_c$ is determined. A differentiated description of these crystal parameters is illustrated in chapter 3 of Stout & Jensen (see above). The details for trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate from the single crystal measurements, especially the atom coordinates, the isotropic thermal parameters, the coordinates of the hydrogen atoms as well as the corresponding isotropic thermal parameters, show that a monoclinic unit cell exists, its cell content of twelve formula units of $C_{48}H_{55}N_6O_8Na_3$.2.5 H$_2$O occurring as a result of two asymmetric units on two-fold positions.

The acentric space group P2$_1$ determined from the single crystal X-ray structure is a common space group for enantiomorphically pure molecules. In this space group there are two general positions which means that for twelve formula units in the unit cell there must be 18 sodium ions and 15 waters in the asymmetric unit.

A pictorial representation of the unit cell of the supramolecular complex of trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate comprising two asymmetric units is shown in FIG. 1.

Based on the single crystal structure solution, the asymmetric unit of the trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate supramolecule comprises six each of ARB and NEPi moieties, 18 sodium atoms, and 15 water molecules. Trisodium [3-((1S,3R)-1-biphenyl-4-ylmethyl-3-ethoxycarbonyl-1-utylcarbamoyl)propionate-(S)-3'-methyl-2'-(pentanoyl{2"-(tetrazol-5-ylate)biphenyl-4'-ylmethyl}amino)butyrate] hemipentahydrate may be considered a sodium supramolecular complex, coordinated by oxygen ligands. These oxygens come from twelve carboxylate groups and eighteen carbonyl groups of the above moieties, and from 13 of the 15 water molecules. The crystal is an infinite 3-dimensional network of these sodium complexes.

Such a compound may also be characterized by an infrared absorption spectrum obtained using Attenuated Total Reflection Fourier Transform Infrared (ATR-FTIR) spectrometer (Nicolet Magna-IR 560) showing the following significant bands, expressed in reciprocal wave numbers (cm$^{-1}$):
2956 (w), 1711 (st), 1637 (st), 1597 (st), 1488 (w), 1459 (m), 1401 (st), 1357 (w), 1295 (m), 1266 (m), 1176 (w), 1085 (m), 1010 (w), 942 (w), 907 (w), 862 (w), 763 (st), 742 (m), 698 (m), 533 (st).

Characteristic to the complex are in particular the following peaks 1711(st), 1637(st), 1597(st) and 1401(st). The error margin for all absorption bands of ATR-IR is ±2 cm$^{-1}$. The intensities of the absorption bands are indicated as follows: (w)=weak; (m)=medium; and (st)=strong intensity.

Such a compound may also be characterized by a Raman spectrum measured by dispersive Raman spectrometer with 785 nm laser excitation source (Kaiser Optical Systems, Inc.) showing the following significant bands expressed in reciprocal wave numbers (cm$^{-1}$):
3061 (m), 2930 (m, broad), 1612 (st), 1523 (m), 1461 (w), 1427 (w), 1287 (st), 1195 (w), 1108 (w), 11053 (w), 1041 (w), 1011 (w), 997 (m), 866 (w), 850 (w), 822 (w), 808 (w), 735 (w), 715 (w), 669 (w), 643 (w), 631 (w), 618 (w), 602 (w), 557 (w), 522 (w), 453 (w), 410 (w), 328 (w).

The error margin for all Raman bands is ±2 cm$^{-1}$. The intensities of the absorption bands are indicated as follows: (w)=weak; (m)=medium; and (st)=strong intensity.

Such a compound may also be characterized by distinct melting properties measured by differential scanning calorimetry (DSC). Using Q1000 (TA Instruments) instrument, the melting onset temperature and the peak maximum temperature for such a complex are observed at 139° C. and 145° C., respectively. The heating rate is 10 K/min.

The second embodiment of the present invention is directed to pharmaceutical compositions comprising a combination, a linked pro-drug or a dual-acting compound, in particular the complex as described herein and at least one pharmaceutically acceptable additive. The details regarding the combination and the complex, including the ARB and the NEPi, are as described above with regard to the first embodiment of the invention.

The pharmaceutical compositions according to the invention can be prepared in a manner known per se and are those suitable for enteral, such as oral or rectal, and parenteral administration to mammals (warm-blooded animals), including man, comprising a therapeutically effective amount of the combination or dual-acting compound, in particular the complex, alone or in combination with at least one pharmaceutically acceptable carrier, especially suitable for enteral or parenteral application. Typical oral formulations include tablets, capsules, syrups, elixirs and suspensions. Typical injectable formulations include solutions and suspensions.

Pharmaceutically acceptable additives suitable for use in the present invention include, without limitation and provided they are chemically inert so that they do not adversely affect the combination or the dual-acting compound, in particular the complex of the present invention, diluents or fillers, disintegrants, glidants, lubricants, binders, colorants and combinations thereof. The amount of each additive in a solid dosage formulation may vary within ranges conventional in the art. Typical pharmaceutically acceptable carriers for use in the formulations described above are exemplified by: sugars, such as lactose, sucrose, mannitol and sorbitol; starches, such as cornstarch, tapioca starch and potato starch; cellulose and derivatives, such as sodium carboxymethyl cellulose, ethyl cellulose and methyl cellulose; calcium phosphates, such as dicalcium phosphate and tricalcium phosphate; sodium sulfate; calcium sulfate; polyvinylpyrrolidone; polyvinyl alcohol; stearic acid; alkaline earth metal stearates, such as magnesium stearate and calcium stearate; stearic acid; vegetable oils, such as peanut oil, cottonseed oil, sesame oil, olive oil and corn oil; non-ionic, cationic and anionic surfactants; ethylene glycol polymers; β-cyclodextrin; fatty alcohols; and hydrolyzed cereal solids, as well as other non-toxic compatible fillers, binders, disintegrants, buffers, preservatives, antioxidants, lubricants, flavoring agents and the like commonly used in pharmaceutical formulations.

Pharmaceutical preparations for enteral or parenteral administration are, e.g., in unit dose forms, such as coated tablets, tablets, capsules or suppositories and also ampoules. These are prepared in a manner which is known per se, e.g., using conventional mixing, granulation, coating, solubilizing or lyophilizing processes. Thus, pharmaceutical compositions for oral use can be obtained by combining the linked pro-drug, combination or dual-acting compound, in particular the complex with solid excipients, if desired, granulating a mixture which has been obtained, and, if required or necessary, processing the mixture or granulate into tablets or coated tablet cores after having added suitable auxiliary substances.

The dosage of the active compounds in the combination or dual-acting compound, in particular the complex can depend on a variety of factors, such as mode of administration, homeothermic species, age and/or individual condition. The projected efficacy in animal disease models ranges from about 0.1 mg/kg/day to about 1000 mg/kg/day given orally, and the projected dose for human treatment ranges from about 0.1 mg/day to about 2000 mg/day. Preferred ranges are from about 40 mg/day to about 960 mg/day of the linked pro-drug, preferably about 80 mg/day to about 640 mg/day. The ARB component is administered in a dosage of from about 40 mg/day to about 320 mg/day and the NEPi component is administered in a dosage of from about 40 mg/day to about 320 mg/day. More specifically, the dosages of ARB/NEPi, respectively, include 40 mg/40 mg, 80 mg/80 mg, 160 mg/160 mg, 320 mg/320 mg, 40 mg/80 mg, 80 mg/160 mg, 160 mg/320 mg, 320 mg/640 mg, 80 mg/40 mg, 160 mg/80 mg and 320 mg/160 mg, respectively. These dosages are "therapeutically effective amounts". Preferred dosages for the linked pro-drug, combination or dual-acting compound, in particular the complex of the pharmaceutical composition according to the present invention are therapeutically effective dosages.

The pharmaceutical compositions may contain in addition another therapeutic agent, e.g., each at an effective therapeutic dose as reported in the art. Such therapeutic agents include:
a) antidiabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; peroxisome proliferator-activated receptor (PPAR) ligands; protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as LAF237;
b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;
c) anti-obesity agents such as orlistat; and
d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; ACE/NEP inhibitors such as omapatrilat, sampatrilat and fasidotril; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors. Most preferred combination partners are diuretics, such as hydrochlorothiazide, and/or calcium channel blockers, such as amlodipine or a salt thereof.

Other specific anti-diabetic compounds are described by Patel Mona in *Expert Opin Investig Drugs,* 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions in addition a therapeu-tically effective amount of another therapeutic agent, preferably selected from anti-diabetics, hypolipidemic agents, anti-obesity agents or anti-hypertensive agents, most preferably from antidiabetics, anti-hypertensive agents or hypolipidemic agents as described above.

The person skilled in the pertinent art is fully enabled to select a relevant test model to prove the efficacy of a combination of the present invention in the hereinbefore and hereinafter indicated therapeutic indications.

Representative studies are carried out with trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate, e.g. applying the following methodology:

The antihypertensive and neutral endopeptidase 24.11 (NEP)-inhibitory activities of trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate is assessed in conscious rats. The blood pressure-lowering effect is evaluated in double-transgenic rats (dTGRs) that overexpress both human renin and its substrate, human angiotensinogen (Bohlender, et al, High human renin hypertension in transgenic rats. Hypertension; 29(1 Pt 2):428-34, 1997). Consequently, these animals exhibit an angiotensin II-dependent hypertension. The NEP-inhibitory effect of trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate is determined in conscious Sprague-Dawley rats infused with exogenous atrial natriuretic peptide (ANP). Potentiation of plasma ANP levels is used as an index of NEP inhibition in vivo. In both models, trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate is administered orally as a powder in gelatin mini capsules. The results are summarized below.

Trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate exhibits a dose-dependent and long-lasting antihypertensive effect after oral administration in conscious dTGRs, a rat model of fulminant hypertension.

Oral administration of trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate rapidly and dose-dependently inhibits NEP with a long duration of action, as reflected by its potentiation of plasma ANP immunoreactivity (ANPir) in conscious Sprague-Dawley rats infused with exogenous ANP.

Antihypertensive Effect In Vivo

The dTGRs are instrumented with radiotelemetry transmitters for continuous measurement of arterial blood pressure and heart rate. Animals are randomly assigned to vehicle (empty capsule) or treatment (at 2, 6, 20 or 60 mg/kg, p.o.) groups. Baseline 24-hr mean arterial pressure (MAP) is approximately 170-180 mmHg in all groups. Trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate dose-dependently reduces MAP. The values obtained from the treatment groups are dose-dependent, and the results from the three highest doses are significantly different from the vehicle controls Inhibition of NEP In Vivo The extent and duration of trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate for NEP inhibition in vivo is assessed with methodologies as described previously (Trapani, et al, CGS 35601 and its orally active prodrug CGS 37808 as triple inhibitors of endothelin-converting enzyme-1, neutral endopeptidase 24.11, and angiotensin-converting enzyme. J Cardiovasc Pharmacol; 44(Suppl 1):S211-5, 2004). Rat ANP(1-28) is infused intravenously at a rate of 450 ng/kg/min in conscious, chronically cannulated, male Sprague-Dawley rats. After one hour of infusion, rats are randomly assigned to one of six groups: untreated control, vehicle (empty capsule) control, or one of four doses of drug (2, 6, 20, or 60 mg/kg, p.o.). ANP infusion is continued for an additional eight hours. Blood samples are collected for measuring plasma ANPir by a commercial enzyme immunoassay kit at −60 min (i.e., before initiating ANP infusion), −30 min (after 30 min of ANP infusion), 0 min ("baseline"; after 60 min of ANP infusion but before dosing with drug or its vehicle), and at 0.25, 0.5, 1, 2, 3, 4, 5, 6, 7, and 8 hr post-dosing.

Before ANP infusion, ANPir is low (0.9-1.4 ng/ml) and similar in all six groups. ANP infusion rapidly (by 30 min) elevates ANPir to ~10 ng/ml. This ANPir level is sustained for the duration of the experiment in the untreated and vehicle control groups. In contrast, trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate rapidly (within 15 min) and dose-dependently augments ANPir. In summary, orally administered LCZ696 rapidly and dose-dependently inhibited NEP with a long duration of action as reflected by the potentiation of plasma ANPir.

The available results indicate an unexpected therapeutic effect of a compound according to the invention.

In a third aspect, the present invention is directed to a method of making a linked pro-drug of an ARB or a pharmaceutically acceptable salt thereof and a NEPi or a pharmaceutically acceptable salt thereof comprising the steps of:

(a) adding an inorganic salt forming agent to a solvent to form a linked pro-drug salt forming solution;

(b) adding the salt forming solution to a mixture of an ARB and a NEPi such that the ARB and NEPi form a linked pro-drug; and (c) isolating the linked pro-drug.

Preferably, the components are added in an equivalent amount.

The inorganic salt forming agent includes, but is not limited to, calcium hydroxide, zinc hydroxide, calcium methoxide, calcium acetate, calcium hydrogen carbonate, calcium formate, magnesium hydroxide, magnesium acetate, magnesium formate and magnesium hydrogen carbonate, sodium hydroxide, sodium methoxide, sodium acetate, sodium formate. The inorganic salt forming agent releases the linking moiety into the solvent such that when an ARB and a NEPi are present a linked pro-drug is formed.

Solvents included in the scope of the present invention include, but are not limited to, solvents in which the ARB, NEPi and inorganic salt forming agent preferably exhibit a lower solubility that allows the linked pro-drug to crystallize. Such solvents may comprise, but are not limited to, water, methanol, ethanol, 2-propanol, ethyl acetate, methyl-t-butylether, acetonitrile, toluene, and methylene chloride and mixtures of such solvents.

The inorganic salt forming agent and the solvent when combined should have a pH which promotes linked pro-drug formation. The pH may be between about 2 and about 6, preferably between about 3 and about 5, most preferably between 3.9 and 4.7.

The linked pro-drug is isolated by crystallization and chromatography. Specific types of chromatography include, e.g., ligand specific resin chromatography, reverse phase resin chromatography and ion-exchange resin chromatography.

A specific example comprises contacting a divalent salt of one component with a mono-valent salt of the other component of the linked pro-drug. Specifically the mixed salt of valsartan and a mono-basic NEPi are synthesized by contacting the calcium salt of valsartan with the sodium salt of the NEPi component. Isolation of the desired mixed salt is carried out by selective crystallization or chromatography using ligand specific resins, reverse phase resins or ion-exchange resins. Similarly this process can be conducted with a monovalent salt of both components, such as the sodium salt of both components.

In another embodiment of this aspect of the invention, a co-crystal of the linked pro-drug is obtained. In a method of making a linked pro-drug co-crystal the inorganic salt forming agent is replaced with a neutral molecule which provides hydrogen binding properties. The solvent may be part of the molecular packing and be trapped in the crystal lattice.

In a preferred embodiment of the third aspect, the present invention is directed to a method of preparing a dual-acting compound comprising
  (a) an angiotensin receptor antagonist;
  (b) a neutral endopeptidase inhibitor (NEPi); and optionally
  (c) a pharmaceutically acceptable cation;
said method comprising the steps of:
  (i) dissolving an angiotensin receptor antagonist and a neutral endopeptidase inhibitor (NEPi) in a suitable solvent;
  (ii) dissolving a basic compound of Cat in a suitable solvent, wherein Cat is a cation;
  (iii) combining the solutions obtained in steps (i) and (ii);
  (iv) precipitation of the solid, and drying same to obtain the dual-acting compound; or alternatively
  obtaining the dual-acting compound by exchanging the solvent(s) employed in steps (i) and (ii) by
  (iva) evaporating the resulting solution to dryness;
  (va) re-dissolving the solid in a suitable solvent;
  (via) precipitation of the solid and drying same to obtain the dual-acting compound.

The details regarding the complex, including the ARB, the NEPi and the cation, are as described above with regard to the first embodiment of the invention.

Preferably, in step (i) the ARB and the NEPi are added in an equivalent molar amount. Both the ARB and the NEPi are preferably used in the free form. The solvent used in step (i) may be any solvent that allows dissolution of both the ARB and the NEPi. Preferred solvents include those mentioned above, namely water, methanol, ethanol, 2-propanol, acetone, ethyl acetate, isopropyl acetate, methyl-t-butylether, acetonitrile, toluene, DMF, NMF and methylene chloride and mixtures of such solvents, such as ethanol-water, methanol-water, 2-propanol-water, acetonitrile-water, acetone-water, 2-propanol-toluene, ethyl acetate-heptane, isopropyl acetate-acetone, methyl-t-butyl ether-heptane, methyl-t-butyl ether-ethanol, ethanol-heptane, acetone-ethyl acetate, acetone-cyclohexane, toluene-heptane, more preferably acetone.

Preferably, in step (ii) the basic compound of Cat is a compound capable of forming a salt with the acidic functionalities of the ARB and the NEPi. Examples include those mentioned above, such as calcium hydroxide, zinc hydroxide, calcium methoxide, calcium ethoxide, calcium acetate, calcium hydrogen carbonate, calcium formate, magnesium hydroxide, magnesium acetate, magnesium formate, magnesium hydrogen carbonate, sodium hydroxide, sodium carbonate, sodium hydrogen carbonate, sodium methoxide, sodium ethoxide, sodium acetate, sodium formate, potassium hydroxide, potassium carbonate, potassium hydrogen carbonate, potassium methoxide, potassium ethoxide, potassium acetate, potassium formate, ammonium hydroxide, ammonium methoxide, ammonium ethoxide, and ammonium carbonate. Perchlorates may also be used. Amine bases or salt forming agents such as those mentioned above may also be used, in particular benzathine, L-arginine, cholin, ethylene diamine, L-lysine or piperazine. Typically an inorganic base is employed with Cat as specified herein. More preferably, the basic compound is (Cat)OH, $(Cat)_2CO_3$, $(Cat)HCO_3$, still more preferably Cat(OH), such as NaOH. The basic compound is employed in an amount of at least 3 equivalents relative to either the ARB or the NEPi, preferably it is employed in stoichiometric amount to obtain the dual-acting compound, in particular the complex with three cations. The solvent used in step (ii) may be any solvent or mixtures of solvents that allow dissolution of Cat(OH). Preferred solvents include water, methanol, ethanol, 2-propanol, acetone, ethyl acetate, isopropyl acetate, methyl-t-butylether, acetonitrile, toluene, and methylene chloride and mixtures of such solvents, more preferably water.

In step (iii) the solutions obtained in steps (i) and (ii) are combined. This can take place by adding the solution obtained in step (i) to the solution obtained in step (ii) or vice versa, preferably, the solution obtained in step (ii) to the solution obtained in step (i).

According to the first alternative, once combined and preferably mixed, the dual-acting compound, in particular the complex precipitates in step (iv). This mixing and precipitation is typically effected by stirring the solutions for an appropriate amount of time such as 20 min to 6 h, preferably 30 min to 3 h, more preferably 2 h, at room temperature. It is advantageous to add seeds of the dual acting compound. This method facilitates precipitation.

In step (iv) according to this first alternative, a co-solvent is typically added. The co-solvent employed is a solvent in which the ARB and the NEPi in the complexed form exhibit a lower solubility that allows the compound to precipitate. Distillation, either continuous or stepwise, with replacement by this co-solvent results in a mixture predominantly of the co-solvent. Preferred solvents include ethanol, 2-propanol, acetone, ethyl acetate, isopropyl acetate, methyl-t-butylether, acetonitrile, toluene, and methylene chloride and mixtures of such solvents, more preferably isopropyl acetate. Preferably, a minimum amount of solvent is employed to facilitate precipitation. The solid is collected, e.g. by filtration, and is dried to obtain the dual-acting compound, in particular the complex in accordance with the present invention. The drying step can be performed at room temperature or elevated temperature such as 30 to 60° C., preferably 30 to 40° C. Reduced pressure can be employed to facilitate removal of the solvent, preferably, drying is effected at ambient pressure or reduced pressure of e.g. 10 to 30 bar, such as 20 bar.

According to a second alternative, once combined and preferably mixed, the dual-acting compound, in particular the complex the mixture preferably forms a clear solution. This mixing is typically effected by stirring the solutions for an appropriate amount of time such as 20 min to 6 h, preferably 30 min to 3 h, more preferably 1 h, at room temperature. If necessary, the temperature may be raised so as to ensure a clear solution.

The obtained mixture is then further treated by solvent exchange to obtain the dual-acting compound, in particular the complex.

In step (iva) according to this second alternative, the solution is preferably evaporated to dryness at elevated temperatures such as >room temperature to 50° C., more preferably 30 to 40° C.

Preferably, in step (va) the solvent or solvent mixture employed is a solvent in which the ARB and the NEPi in the complexed form exhibit a lower solubility that allows the dual-acting compound, in particular the complex to precipitate. Preferred solvents include the ones mentioned above for step (i), such as water, ethanol, 2-propanol, acetone ethyl acetate, isopropyl acetate, methyl-t-butylether, acetonitrile, toluene, and methylene chloride and mixtures of such solvents, more preferably isopropyl acetate. Preferably, a minimum amount of solvent or solvent mixture is employed to facilitate precipitation.

In step (via) precipitation can take place at room temperature. It can be effected by leaving the mixture standing or by agitating the mixture, preferably by agitating it. This is preferably effected by stirring and/or sonication. After precipitation, the solid is collected, e.g. by filtration, and is dried to obtain the compound in accordance with the present invention. The drying step can be performed at room temperature or elevated temperature such as 30 to 60° C., preferably room temperature. Reduced pressure can be employed to facilitate removal of the solvent, preferably, drying is effected at ambient pressure.

In a fourth aspect, this invention is directed to a method of treating or preventing a disease or condition, such as hypertension, heart failure (acute and chronic) congestive heart failure, left ventricular dysfunction and hypertrophic cardiomyopathy, diabetic cardiac myopathy, supraventricular and ventricular arrhythmias, atrial fibrillation, atrial flutter, detrimental vascular remodeling, myocardial infarction and its sequelae, atherosclerosis, angina (unstable or stable), renal insufficiency (diabetic and non-diabetic), heart failure, angina pectoris, diabetes, secondary aldosteronism, primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, other vascular disorders, such as migraine, peripheral vascular disease, Raynaud's disease, luminal hyperplasia, cognitive dysfunction (such as Alzheimer's), glaucoma and stroke comprising administering the afore-mentioned combination, linked pro-drug or the dual-acting compound, in particular the complex to a subject in need of such treatment.

The combination, linked pro-drug or the dual-acting compound, in particular the complex of the first embodiment may be administered alone or in the form of a pharmaceutical composition according to the second embodiment.

Information regarding dosing, i.e., the therapeutically effective amount, etc., is the same regardless of how the combination, linked pro-drug or he dual-acting compound, in particular the complex is administered.

The combination, linked pro-drug or the dual-acting compound, in particular the complex is beneficial over a combination of ARBs or neutral endopeptidase inhibitors alone or other ARB/NEPi combinations with regard to use as first line therapy, ease of formulation and ease of manufacture.

Specific embodiments of the invention will now be demonstrated by reference to the following examples. It should be understood that these examples are disclosed solely by way of illustrating the invention and should not be taken in any way to limit the scope of the present invention.

EXAMPLE 1

Preparation of [valsartan ((2R,4S)-5-biphenyl-4-yl-4-(3-carboxy-propionylamino)-2-methyl-pentanoic acid ethyl ester)]$Na_3$.2.5 $H_2O$ The dual-acting compound of valsartan and (2R,4S)-5-biphenyl-4-yl-4-(3-carboxy-propionylamino)-2-methyl-pentanoic acid ethyl ester is prepared by dissolving 0.42 g of (2R,4S)-5-biphenyl-4-yl-4-(3-carboxy-propionylamino)-2-methyl-pentanoic acid ethyl ester free acid (~95% purity) and 0.41 g of valsartan free acid in 40 ml acetone. Separately, 0.111 g of NaOH are dissolved in 7 ml $H_2O$. The two solutions are combined and stirred at room temperature for 1 hour and a clear solution was obtained. The solution is evaporated at 35° C. to yield a glassy solid. The glassy solid residue is then charged with 40 ml acetone and the resulting mixture is stirred and sonicated until precipitation occurred (~5 minutes). The precipitate was filtered and the solid is dried at room temperature in open air for 2 days until a constant mass of the crystalline solid is obtained.

Characterization by various methods could confirm the presence of both valsartan and (2R,4S)-5-biphenyl-4-yl-4-(3-carboxy-propionylamino)-2-methyl-pentanoic acid ethyl ester and complex formation in contrast to a simple physical mixture. Significant spectral peaks for the complex are observed e.g. in the XRPD, IR, and Raman spectroscopy which are not present for the physical mixture. See below for details on the characterization.

EXAMPLE 2

Alternative Preparation of [valsartan ((2R,4S)-5-biphenyl-4-yl-4-(3-carboxy-propionylamino)-2-methyl-pentanoic acid ethyl ester)]$Na_3$.2.5 $H_2O$ The dual acting compound of valsartan and (2R,4S)-5-biphenyl-4-yl-4-(3-carboxy-propionylamino)-2-methyl-pentanoic acid ethyl ester is prepared by dissolving 22.96 mmol of (2R,4S)-5-biphenyl-4-yl-4-(3-carboxy-propionylamino)-2-methyl-pentanoic acid ethyl ester free acid (~95% purity) and valsartan (10.00 g; 22.96 mmol) in acetone (300 mL). The suspension is stirred at room temperature for 15 min to obtain a clear solution. A solution of NaOH (2.76 g; 68.90 mmol) in water (8 mL) water is then added to this solution over a period of 10 min. Solids start to precipitate in 10 min. Alternatively, precipitation can be induced by seeding. The suspension is stirred at 20-25° C. for 2 h. This suspension is concentrated at 15-30° C. under reduced pressure (180-250 mbar) to a batch volume of ~150 mL. Isopropyl acetate (150 mL) is then added to the batch and the suspension is concentrated again at 15-30° C. under reduced pressure (180-250 mbar) to a batch volume of ~150 mL. This operation (addition of 150 mL of isopropyl acetate to the batch and concentration) is repeated once again. The suspension is stirred at 20-25° C. for 1 h. The solids are collected by filtration under nitrogen over a Büchner funnel, washed with isopropyl acetate (20 mL), and dried at 35° C. under reduced pressure (20 mbar) to afford the compound.

Characterization revealed the same product as in Example 1.

EXAMPLE 3

Alternative Preparation of [valsartan ((2R,4S)-5-biphenyl-4-yl-4-(3-carboxy-propionylamino)-2-methyl-pentanoic acid ethyl ester)]Na$_3$.2.5 H$_2$O Using Seeding A reactor is charged with 2.00 kg (2,323 mmol) of AHU377 calcium salt and 20 L of isopropyl acetate. The suspension is stirred at 23±3° C., and 4.56 L of 2 N HCl was added. The mixture is stirred at 23±3° C. for 15 min to obtain a clear two-phase solution. The organic layer is separated and washed with 3×4.00 L of water. The organic layer is concentrated at 30-100 mbar and 22±5° C. to ~3.5 L (3.47 kg) of AHU377 free acid isopropyl acetate solution as a colorless solution.

To the above reactor containing ~3.5 L (3.47 kg) of AHU377 free acid isopropyl acetate solution is added 1.984 kg (4,556 mmol) of Valsartan and 40 L of acetone. The reaction mixture is stirred at 23±3° C. to obtain a clear solution which is filtered into a reactor. To the reaction mixture is added a solution of 547.6 g (13,690 mmol) of NaOH in 1.0 L of water at 23±3° C. (which was pre-cooled to 20±5° C. and in-line filtered) over a period of 15-30 min while maintaining the internal temperature at 20-28° C. (slightly exothermic). The flask is rinsed with 190 mL of water and added into the reaction mixture. The reaction mixture is stirred at 23±3° C. for 15 min and a slurry of 4.0 g of [valsartan ((2R,4S)-5-biphenyl-4-yl-4-(3-carboxy-propionylamino)-2-methyl-pentanoic acid ethyl ester)]Na$_3$.2.5 H$_2$O seeds in 50 mL of isopropyl acetate is added. The mixture is stirred at 23±3° C. for 2 h to obtain a suspension. The suspension is heated to an internal temperature at 40±3° C. over a period of 20 min and 20 L of isopropyl acetate is added over a period of 20 min while maintaining the internal temperature at 40±3° C. The suspension is stirred at this temperature for an additional 30 min. The mixture is concentrated at an internal temperature at 35±5° C. (T$_j$ 45±5° C.) under reduced pressure (200-350 mbar) to ~35 L of a white slurry (solvent collected: ~25 L). Then 30 L of isopropyl acetate is added the mixture is concentrated at an internal temperature at 35±5° C. (T$_j$ 45±5° C.) under reduced pressure (100-250 mbar) to ~30 L of a white slurry (solvent collected: ~40 L).

Again 40 L of isopropyl acetate is added and the mixture is concentrated at an internal temperature at 35±5° C. (T$_j$ 45±5° C.) under reduced pressure (100-200 mbar) to ~30 L of a white slurry (solvent collected: ~30 L). The reaction mixture is cooled to 23±3° C. over ~20 min and stirred at this temperature for an additional 3 h. The solid is collected by filtration under nitrogen over a polypropylene pad on Büchner funnel. The solid is washed with 2×5 L of isopropyl acetate and dried at 35° C. under reduced pressure (20 mbar) until isopropyl acetate content <0.5% to afford the above product as a white solid.

Characterization revealed the same product as in Example 1.

X-ray Powder Diffraction

Calculation of the interlattice plane intervals from the X-ray powder pattern taken with a Scintag XDS2000 powder diffractometer for the most important lines for the sample give the following results:

d in [Å]: 21.2(s), 17.0(w), 7.1(s), 5.2(w), 4.7(w), 4.6(w), 4.2(w), 3.5(w), 3.3(w)

The error margin for all interlattice plane intervals is ±0.1 Å. The intensities of the peaks are indicated as follows: (w)=weak; (m)=medium; and (st)=strong.

Average values 2Θ in [°] are indicated (error limit of ±0.2)

4.5, 5.5, 5.6, 9.9, 12.8, 15.7, 17.0, 17.1, 17.2, 18.3, 18.5, 19.8, 21.5, 21.7, 23.2, 23.3, 24.9, 25.3, 27.4, 27.9, 28.0, 30.2.

Elemental Analysis

Elemental analysis gives the following measured values of the elements present in the sample. The findings of the elemental analysis, within the error limits, correspond to the overall formula of (C$_{48}$H$_{55}$N$_6$O$_8$Na$_3$).2.5H$_2$O

| Found | C: 60.05% | H: 6.24% | N: 8.80% |
|---|---|---|---|
| Calculated* | C: 60.18% | H: 6.31% | N: 8.77% |

Infrared Spectroscopy

The infrared absorption spectrum for the sample obtained using Attenuated Total Reflection Fourier Transform Infrared (ATR-FTIR) spectrometer (Nicolet Magna-IR 560) shows the following significant bands, expressed in reciprocal wave numbers (cm$^{-1}$):

2956 (w), 1711 (st), 1637 (st), 1597 (st), 1488 (w), 1459 (m), 1401 (st), 1357 (w), 1295 (m), 1266 (m), 1176 (w), 1085 (m), 1010 (w), 942 (w), 907 (w), 862 (w), 763 (st), 742 (m), 698 (m), 533 (st).

The error margin for all absorption bands of ATR-IR is ±2 cm$^{-1}$.

The intensities of the absorption bands are indicated as follows: (w)=weak; (m)=medium; and (st)=strong intensity.

Raman Spectroscopy

Raman spectrum of the sample measured by dispersive Raman spectrometer with 785 nm laser excitation source (Kaiser Optical Systems, Inc.) shows the following significant bands expressed in reciprocal wave numbers (cm$^{-1}$):

3061 (m), 2930 (m, broad), 1612 (st), 1523 (m), 1461 (w), 1427 (w), 1287 (st), 1195 (w), 1108 (w), 11053 (w), 1041 (w), 1011 (w), 997 (m), 866 (w), 850 (w), 822 (w), 808 (w), 735 (w), 715 (w), 669 (w), 643 (w), 631 (w), 618 (w), 602 (w), 557 (w), 522 (w), 453 (w), 410 (w), 328 (w).

The error margin for all Raman bands is ±2 cm$^{-1}$.

The intensities of the absorption bands are indicated as follows: (w)=weak; (m)=medium; and (st)=strong intensity.

High Resolution CP-MAS $^{13}$C NMR Spectroscopy

The samples are investigated by high resolution CP-MAS (Cross Polarization Magic Angle Spinning) $^{13}$C NMR spectroscopy using a Bruker-BioSpin AVANCE 500 NMR spectrometer equipped with a 300 Watt high power $^1$H, two 500 Watt high power X-amplifiers, necessary high power preamplifiers, a "MAS" controller and a 4 mm BioSolids high resolution Bruker probe.

Each sample is packed in a 4 mm $ZrO_2$ rotor. Critical experimental parameters are 3 msec $^{13}$C contact times, 12 KHz spinning speed at the magic angle, a "ramped" contact time, using a "SPINAL64" $^1$H decoupling scheme, a recycle delay of 10 secs and 1024 scans at 293 deg K. The chemical shifts are referenced with respect to an external Glycine carbonyl at 176.04 ppm.

High resolution CP-MAS $^{13}$C NMR shows the following significant peaks (ppm):
179.0, 177.9 177.0, 176.7, 162.0, 141.0, 137.2, 129.6, 129.1, 126.7, 125.3, 64.0, 61.5, 60.4, 50.2, 46.4, 40.6, 38.6, 33.5, 32.4, 29.8, 28.7, 22.3, 20.2, 19.1, 17.8, 16.8, 13.1, 12.1, 11.1.

A physical mixture of individual Na salts of Valsartan and (2R,4S)-5-biphenyl-4-yl-4-(3-carboxy-propionylamino)-2-methyl-pentanoic acid ethyl ester revealed a simple inert mixture of the two salts. However, the sample of the complex prepared in Example 1 exhibited distinctly different spectral features in comparison to a 1:1 mixture of the sodium salts.

DSC and TGA

As measured by differential scanning calorimetry (DSC) using Q1000 (TA Instruments) instrument, the melting onset temperature and the peak maximum temperature for the sample is observed at 139° C. and 145° C., respectively.

As shown by DSC and thermogravimetric analysis (TGA), upon heating, the water of hydration is released in two steps: the first step occurs below 100° C. and the second step above 120° C.

Both DSC and TGA instruments are operated at a heating rate of 10 K/min.

EXAMPLE 4

Preparation of Linked Pro-Drug of Scheme (1)

Linked pro-drug of valsartan calcium salt and (2R,4S)-5-biphenyl-4-yl-4-(3-carboxy-propionylamino)-2-methyl-pentanoic acid ethyl ester is prepared at room temperature by dissolving 114 mg of the calcium salt of valsartan and 86 mg of (2R,4S)-5-biphenyl-4-yl-4-(3-carboxy-propionylamino)-2-methyl-pentanoic acid ethyl ester free acid in 2 mL methanol, followed by methanol evaporation. The glassy solid residue is then charged with 3 mL of acetonitrile and equilibrated by 10 min. sonication, followed by 20 hours of magnetic stirring. Approximately 120 mg of white solids are collected by filtration. Liquid chromatography (LC) and elemental analysis indicate 1:1 ratio between (2R,4S)-5-biphenyl-4-yl-4-(3-carboxy-propionylamino)-2-methyl-pentanoic acid ethyl ester and valsartan. The sample is amorphous by X-ray powder diffraction.

Preparation of Linked Pro-Drug of Scheme (2)

Linked pro-drug of valsartan calcium salt and (2R,4S)-5-biphenyl-4-yl-4-(3-carboxy-propionylamino)-2-methyl-pentanoic acid ethyl ester and Tris is prepared at room temperature by dissolving 57 mg of the calcium salt of valsartan, 43 mg of (2R,4S)-5-biphenyl-4-yl-4-(3-carboxy-propionylamino)-2-methyl-pentanoic acid ethyl ester free acid, and 12.6 mg of tris(hydroxymethyl)aminomethane (Tris) in 2 mL methanol, followed by methanol evaporation. The glassy solid residue is then charged with 3 mL of acetonitrile and equilibrated by 10 min. sonication, followed by 20 hours of magnetic stirring. Approximately 83 mg of white solids are collected by filtration. LC and elemental analysis indicate 1:1 ratio between (2R,4S)-5-biphenyl-4-yl-4-(3-carboxy-propionylamino)-2-methyl-pentanoic acid ethyl ester and valsartan. The sample is amorphous by X-ray powder diffraction.

While the invention has been described above with reference to specific embodiments thereof, it is apparent that many changes, modifications, and variations can be made without departing from the inventive concept disclosed herein. Accordingly, it is intended to embrace all such changes, modifications and variations that fall within the spirit and broad scope of the appended claims. All patent applications, patents, and other publications cited herein are incorporated by reference in their entirety.

What is claimed is:

1. An amorphous solid form of a compound consisting of anionic (S)—N-valeryl-N-{[2'-(1H-tetrazole-5-yl)-biphenyl-4-yl]-methyl}-valine, anionic (2R,4S)-5-biphenyl-4-yl-4-(3-carboxy-propionylamino)-2-methyl-pentanoic acid ethyl ester, and sodium cations in a 1:1:3 molar ratio.

2. A pharmaceutical composition comprising the amorphous solid form according to claim 1 and at least one pharmaceutically acceptable excipient.

* * * * *